US008821385B2

(12) United States Patent
Naito

(10) Patent No.: US 8,821,385 B2
(45) Date of Patent: Sep. 2, 2014

(54) ENDOSCOPE AND HELICAL ROTATION MEMBER ATTACHED TO INSERTION UNIT OF THIS ENDOSCOPE

(71) Applicant: Olympus Medical Systems Corp., Tokyo (JP)

(72) Inventor: Kimihiko Naito, Kawasaki (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/017,405

(22) Filed: Sep. 4, 2013

(65) Prior Publication Data
US 2014/0058203 A1    Feb. 27, 2014

Related U.S. Application Data

(63) Continuation of application No. PCT/JP2013/052765, filed on Feb. 6, 2013.

(30) Foreign Application Priority Data

Mar. 21, 2012  (JP) ................................ 2012-064448

(51) Int. Cl.
| | | |
|---|---|---|
| *A61B 1/00* | (2006.01) | |
| *A61B 1/01* | (2006.01) | |
| *A61B 1/06* | (2006.01) | |
| *G02B 23/24* | (2006.01) | |

(52) U.S. Cl.
CPC ........... *A61B 1/0016* (2013.01); *A61B 1/00071* (2013.01); *A61B 1/00158* (2013.01); *A61B 1/00135* (2013.01); *A61B 1/0008* (2013.01); *A61B 1/00112* (2013.01); *A61B 1/0669* (2013.01); *A61B 1/01* (2013.01); *G02B 23/24* (2013.01); *A61B 1/00045* (2013.01); *A61B 1/00156* (2013.01); *G02B 23/2476* (2013.01); *A61B 1/00101* (2013.01)
USPC ............ 600/114; 600/137; 600/104; 600/106

(58) Field of Classification Search
CPC ............ A61B 1/00071; A61B 1/0008; A61B 1/00101; A61B 1/00112; A61B 1/00135; A61B 1/00156; A61B 1/00158; A61B 1/01; G02B 23/24; G02B 23/2476

USPC .................................. 600/114, 137, 104, 106
See application file for complete search history.

(56) References Cited

U.S. PATENT DOCUMENTS

2005/0272976 A1 * 12/2005 Tanaka et al. ................. 600/114
2007/0161862 A1 *  7/2007 Yokoi et al. ................... 600/175
(Continued)

FOREIGN PATENT DOCUMENTS

| DE | 2804015 | * | 8/1979 |
| JP | 55-42657 A | | 3/1980 |

(Continued)

OTHER PUBLICATIONS

English language translation of International Search Report PCT/JP2013/052765 dated Mar. 5, 2013.

*Primary Examiner* — John P Leubecker
*Assistant Examiner* — Arnaldo Torres Diaz
(74) *Attorney, Agent, or Firm* — Scully, Scott, Murphy & Presser, P.C.

(57) ABSTRACT

An insertion apparatus includes insertion unit, a rotation drive mechanism, a first rotation member which is arranged inside the insertion unit and rotates by the rotation drive mechanism, a second rotation member which is attached to an outer peripheral surface of the insertion unit and is adjacent to the first rotation member, and a helical rotation member which is rotatable in accordance with rotation of the second rotation member. The insertion apparatus include a magnetic force generation mechanism which generates a magnetic force that enables the first rotation member and the second rotation member to be attracted to and coupled and enables the second rotation member to rotate follow rotation of first rotation member. The magnetic force generation mechanism is arranged at a tubular end portion of the first rotation member and a tubular end portion of the second rotation member adjacent to the end portion.

12 Claims, 9 Drawing Sheets

(56) References Cited

U.S. PATENT DOCUMENTS

| | | | |
|---|---|---|---|
| 2007/0249901 A1* | 10/2007 | Ohline et al. | 600/117 |
| 2008/0146875 A1* | 6/2008 | Noguchi et al. | 600/117 |
| 2008/0265705 A1* | 10/2008 | Kinoshita | 310/156.44 |
| 2008/0281188 A1* | 11/2008 | Aoki et al. | 600/424 |
| 2010/0001592 A1* | 1/2010 | Kawano et al. | 310/12.14 |
| 2013/0184526 A1* | 7/2013 | Takizawa et al. | 600/109 |
| 2013/0245398 A1* | 9/2013 | Yokoi et al. | 600/302 |
| 2013/0345506 A1* | 12/2013 | Lien et al. | 600/109 |

FOREIGN PATENT DOCUMENTS

| | | | | |
|---|---|---|---|---|
| JP | 2005-253892 A | | 9/2005 | |
| JP | 2005-329001 A | | 12/2005 | |
| JP | 2010082414 A | * | 4/2010 | |
| WO | WO 2005/087082 A1 | | 9/2005 | |
| WO | WO 2008041809 A1 | * | 4/2008 | A61B 1/05 |

\* cited by examiner

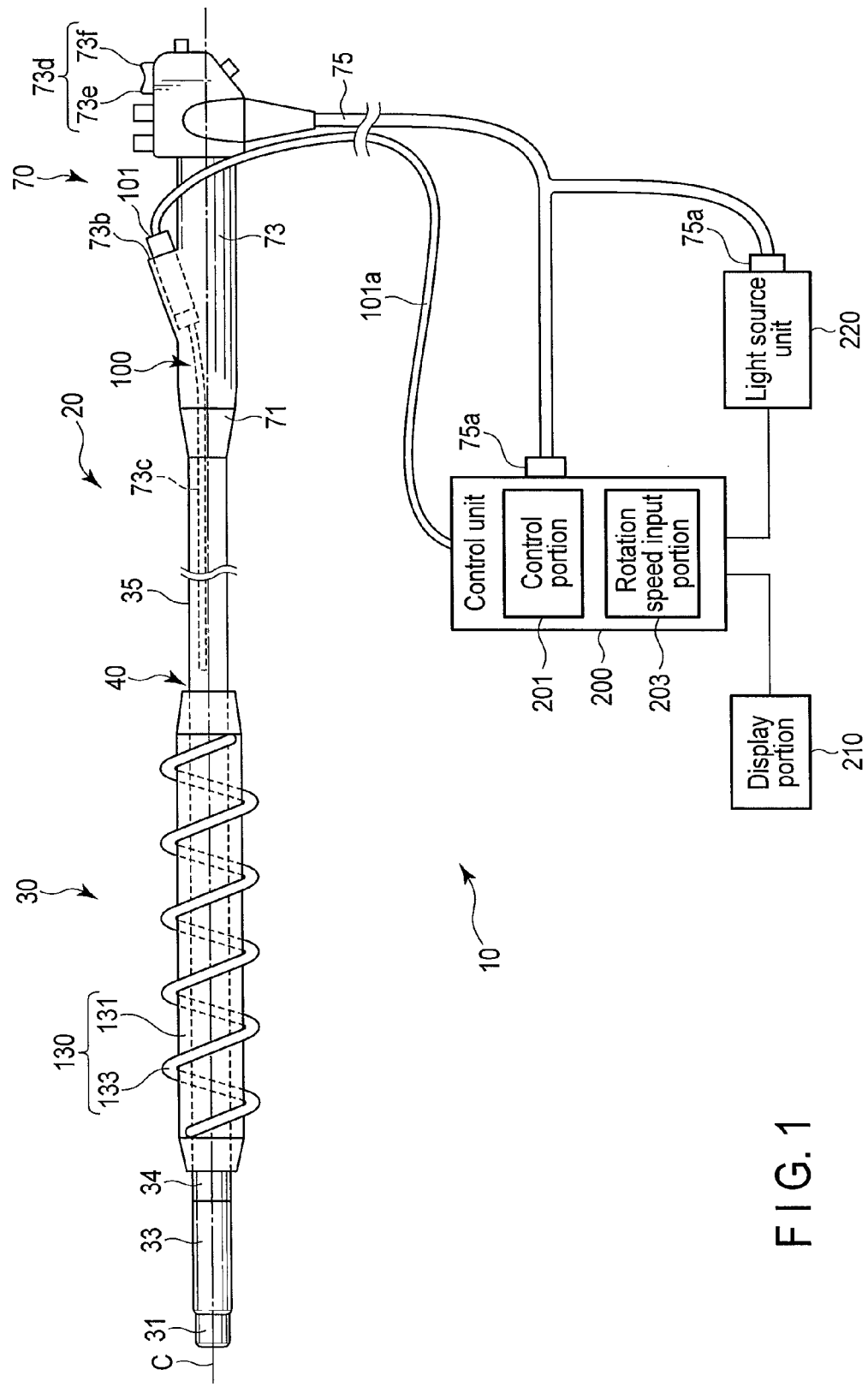
F I G. 1

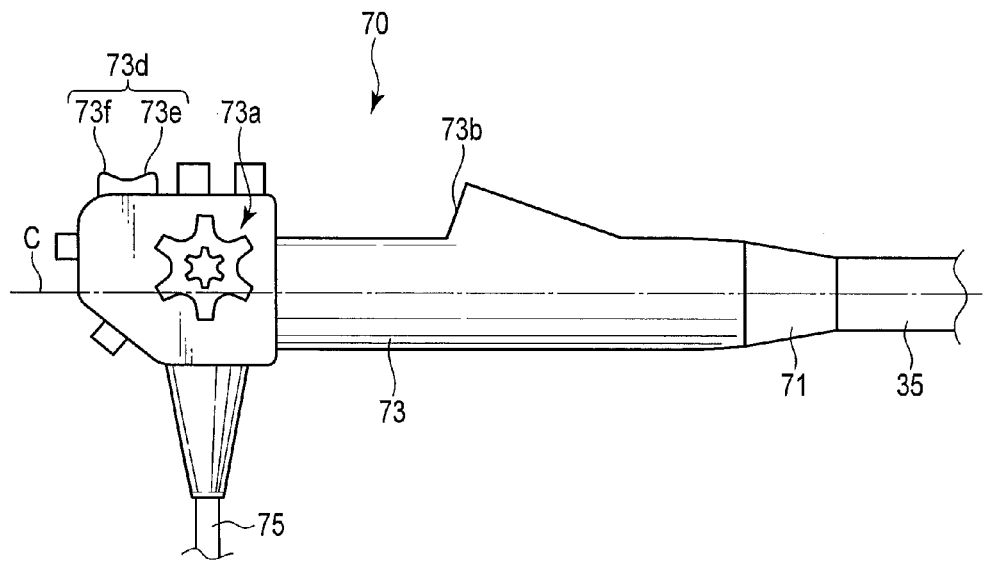
F I G. 2
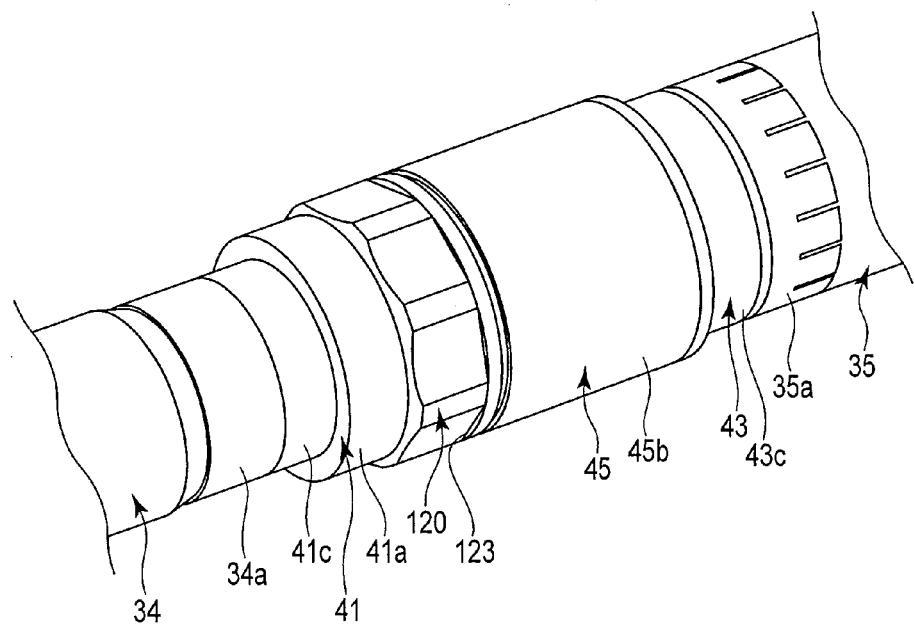
F I G. 3A

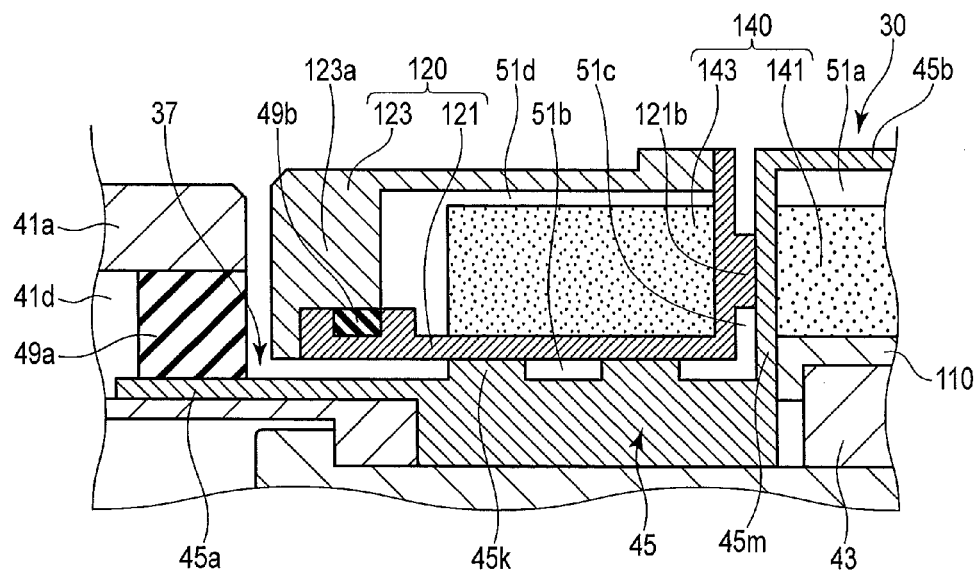
F I G. 3C
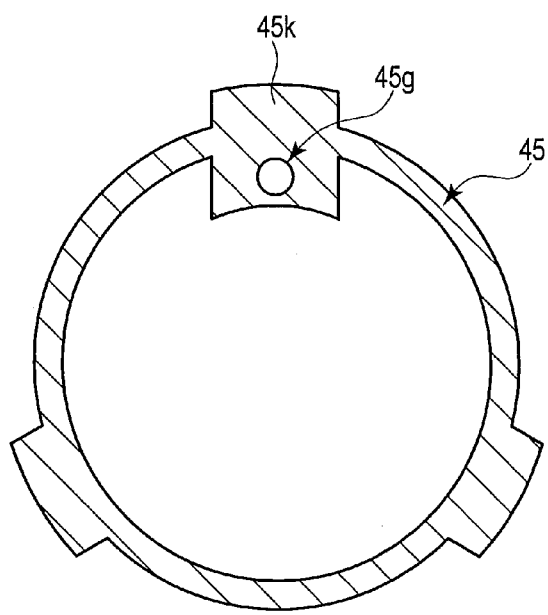
F I G. 3D

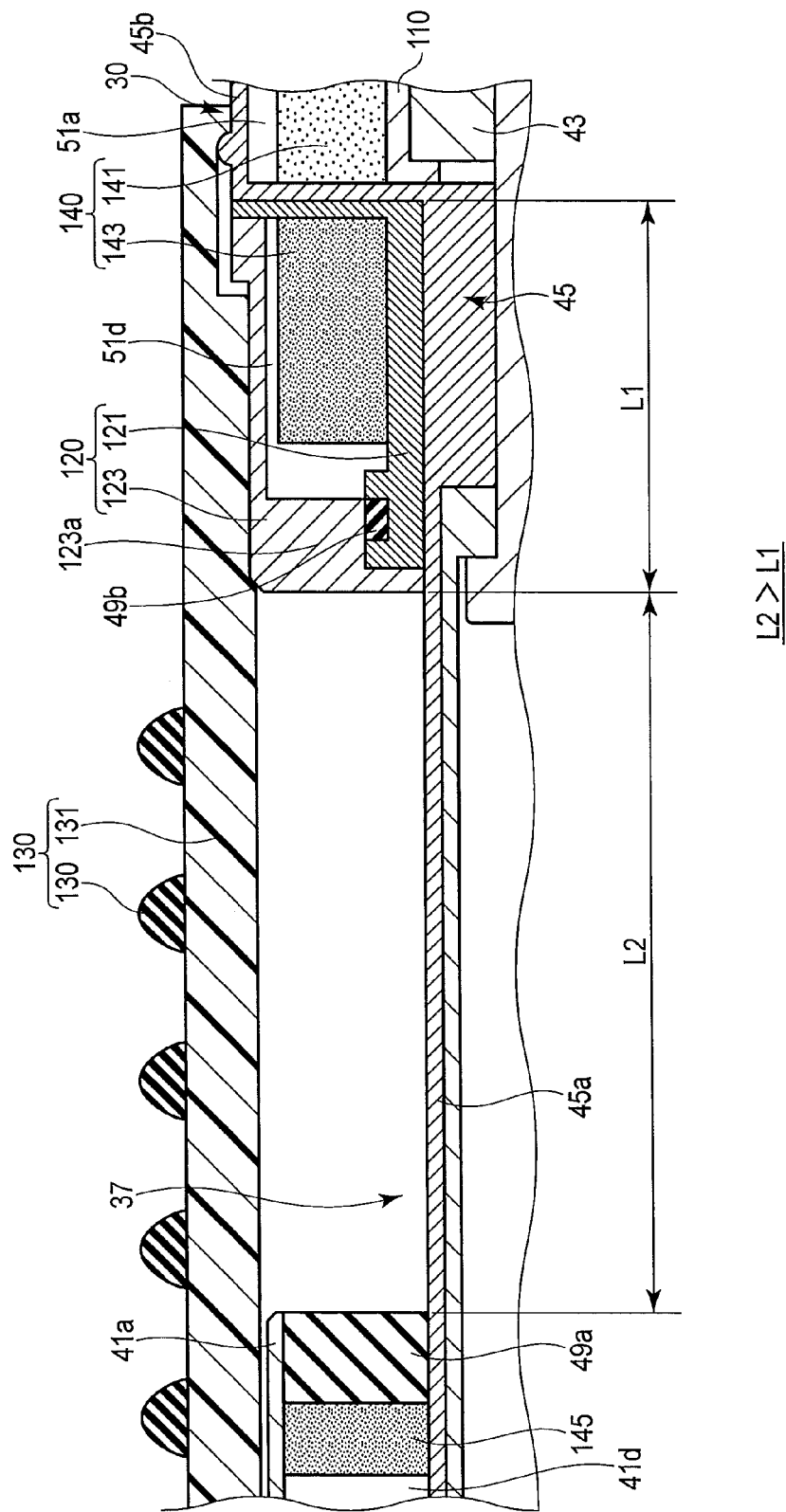
F I G. 6A

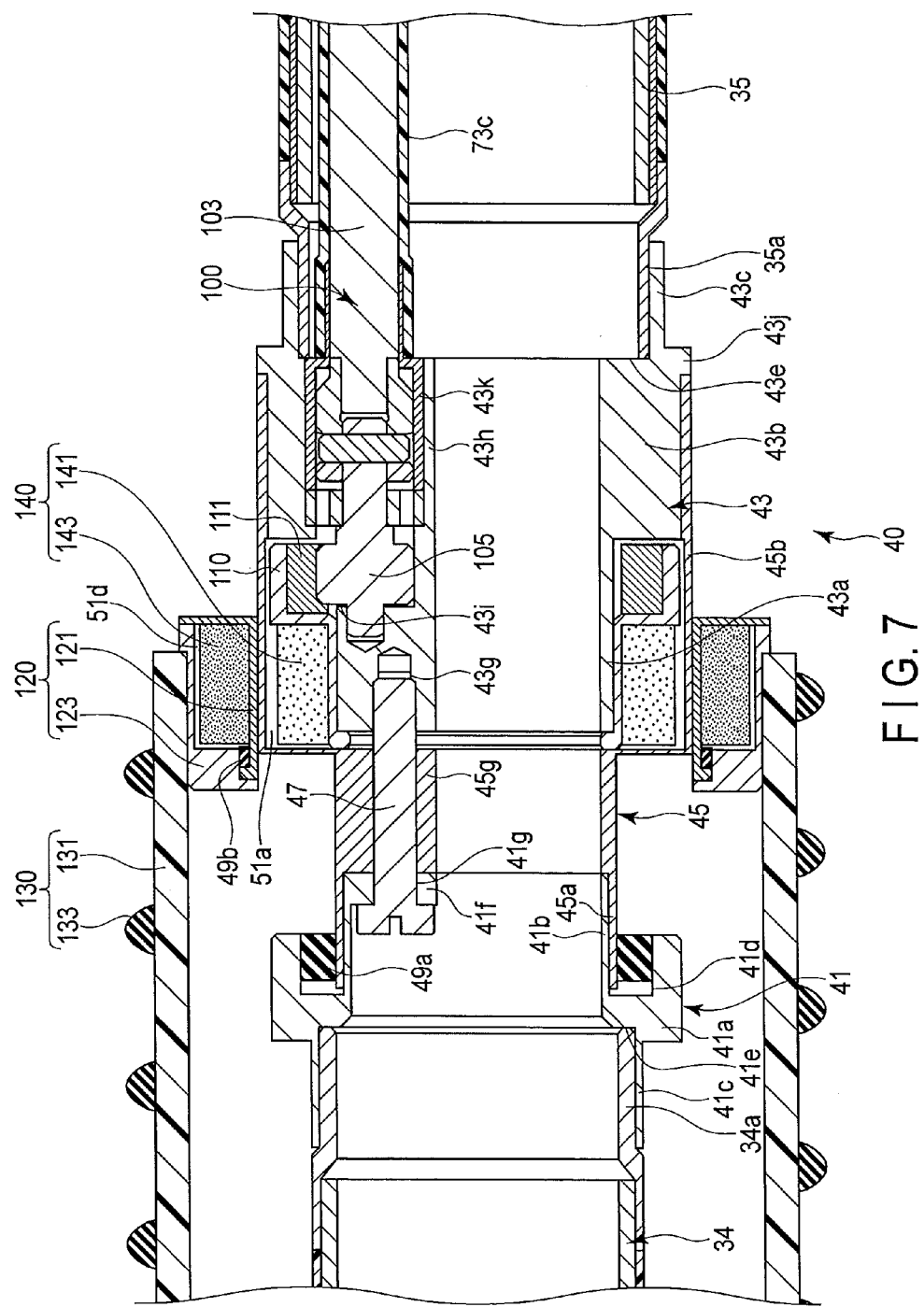
F I G. 7

ENDOSCOPE AND HELICAL ROTATION MEMBER ATTACHED TO INSERTION UNIT OF THIS ENDOSCOPE

CROSS-REFERENCE TO RELATED APPLICATIONS

This application is a Continuation Application of PCT Application No. PCT/JP2013/052765, filed Feb. 6, 2013 and based upon and claiming the benefit of priority from prior Japanese Patent Application No. 2012-064448, filed Mar. 21, 2012, the entire contents of all of which are incorporated herein by reference.

BACKGROUND OF THE INVENTION

1. Field of the Invention

The present invention relates to an endoscope having an insertion unit to which a helical rotation member having a helical fin portion is attached and a helical rotation member that is attached to the insertion unit of this endoscope.

2. Description of the Related Art

For example, Jpn. Pat. Appln. KOKAI Publication No. 2005-253892 discloses an endoscope. This endoscope has an insertion unit that is inserted into a lumen and a helical rotation member having a cylindrical shape that is attached to an outer peripheral surface of the insertion unit so that it can freely rotate in a peripheral direction of a central axis of the insertion unit. Further, the endoscope has an outer magnet secured to an inner peripheral surface of the helical rotation member and a rod-shaped inner magnet arranged inside the insertion unit.

The helical rotation member has a main body portion that is extended along an axial direction of the insertion unit and an inner peripheral surface of the main body is appressed against an outer peripheral surface of the insertion unit and a fin portion that is arranged on an outer peripheral surface of the main body and is helically arranged in the periaxial direction of the insertion unit.

The outer magnet has a ring-like shape. The outer magnet is arranged on the main body portion of the helical rotation member. In the outer magnet, N poles and S poles are alternately arranged along a circumferential direction of the outer magnet.

In the inner magnet, one N pole and one S pole are arranged along a circumferential direction of the inner magnet. The inner magnet is arranged inside the outer magnet. The inner magnet is connected with a motor through a flexible shaft and rotated by the motor.

When the inner magnet rotates, the outer magnet and the inner magnet attract or repel each other, and thereby the outer magnet rotates. When the outer magnet rotates, the main body portion rotates. When the main body portion rotates, the fin portion also rotates, the fin portion engages with an inner wall of the lumen, and an insertion (propulsive) force or removal force acts on the insertion unit. As a result, the insertion unit moves forward or backward in the lumen. As the inner wall of the lumen, for example, a gathered and folded inner wall surface of a large intestine is shown.

BRIEF SUMMARY OF THE INVENTION

An aspect of an endoscope of the present invention includes an insertion unit which is inserted into a lumen and has a longitudinal axis; a rotation drive mechanism which is arranged inside the insertion unit; a tubular first rotation member which is arranged inside the insertion unit, coupled with the rotation drive mechanism, and rotates around the longitudinal axis by the rotation drive mechanism; a tubular second rotation member which is attached to an outer peripheral surface of the insertion unit in such a manner that the second rotation member is adjacent to the first rotation member and a central axis of the first rotation member and a central axis of the second rotation member are coaxially arranged each other, and rotates around the longitudinal axis; a helical rotation member comprising: a tubular main body portion which allows the insertion unit to be inserted therethrough and is rotatable around the longitudinal axis in accordance with rotation of the second rotation member; and a fin portion which is arranged on an outer peripheral surface of the main body portion and also helically arranged around the longitudinal axis; and a magnetic force generation mechanism which is arranged in each of the first rotation member and the second rotation member and generates a magnetic force that enables the first rotation member and the second rotation member to be attracted to and coupled with each other and a magnetic force which enables the second rotation member to rotate in accordance with rotation of the first rotation member when the first rotation member rotates in a state that the first rotation member and the second rotation member are attracted to each other, wherein the magnetic force generation mechanism is arranged at a tubular end portion of the first rotation member and a tubular end portion of the second rotation member adjacent to the end portion of the first rotation member.

An aspect of a helical rotation of the present invention includes a helical rotation member which is attached to an insertion unit of an endoscope and configured to be inserted into a lumen, the endoscope comprising: the insertion unit which is inserted into the lumen and has a longitudinal axis; a rotation drive mechanism which is arranged inside the insertion unit; a tubular first rotation member which is arranged inside the insertion unit, coupled with the rotation drive mechanism, and rotates around the longitudinal axis by the rotation drive mechanism; a tubular second rotation member which is attached to an outer peripheral surface of the insertion unit in such a manner that the second rotation member is adjacent to the first rotation member and a central axis of the first rotation member and a central axis of the second rotation member are coaxially arranged each other, and rotates around the longitudinal axis; and a magnetic force generation mechanism which is arranged in each of the first rotation member and the second rotation member and generates a magnetic force that enables the first rotation member and the second rotation member to be attracted to and coupled with each other and a magnetic force which enables the second rotation member to rotate in accordance with rotation of the first rotation member when the first rotation member rotates in a state that the first rotation member and the second rotation member are attracted to each other, wherein the helical rotation member comprises: a tubular main body portion which allows the insertion unit to be inserted therethrough and is rotatable around the longitudinal axis in accordance with rotation of the second rotation member, and fixed to the second rotation member; and a fin portion which is arranged on an outer peripheral surface of the main body portion and helically arranged around the longitudinal axis.

An aspect of a helical rotation of the present invention includes helical rotation member which is attached to an insertion unit of an endoscope and configured to be inserted into a lumen, the endoscope comprising: the insertion unit which is inserted into the lumen and has a longitudinal axis; a rotation drive mechanism which is arranged inside the insertion unit; a tubular first rotation member which is arranged in the insertion unit, coupled with the rotation drive mechanism, and rotates around the longitudinal axis by the rotation drive mechanism; a tubular second rotation member which is attached to an outer peripheral surface of the insertion unit in such a manner that the second rotation member is adjacent to the first rotation member and a central axis of the first rotation member and a central axis of the second rotation member are coaxially arranged each other, and rotates around the longitudinal axis; and a magnetic force generation mechanism which is arranged in each of the first rotation member and the second rotation member and generates a magnetic force that enables the first rotation member and the second rotation member to be attracted to and coupled with each other and a magnetic force which enables the second rotation member to rotate in accordance with rotation of the first rotation member when the first rotation member rotates in a state that the first rotation member and the second rotation member are attracted to each other, wherein the helical rotation member comprises: a tubular main body portion which allows the insertion unit to be inserted therethrough and is rotatable around the longitudinal axis in accordance with rotation of the second rotation member, and integrally formed with the second rotation member; and a fin portion which is arranged on an outer peripheral surface of the main body portion and helically arranged around the longitudinal axis.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic block diagram of an endoscopic system according to a first embodiment of the present invention;

FIG. 2 is a side elevation of an operation unit seen from a bending operation unit side;

FIG. 3A is a perspective view showing a coupling configuration of a proximal end portion of a passive bending portion and a distal end portion of a flexible tube portion;

FIG. 3C is an enlarged view of a periphery of a frame 3C shown in FIG. 3B;

FIG. 3D is a cross-sectional view of a cylindrical member in a protruding portion;

FIG. 6A is a view showing a first modification of a first embodiment;

FIG. 7 is a cross-sectional view showing a coupling configuration of a proximal end portion of a passive bending portion and a distal end portion of a flexible tube portion and a configuration 2 of an embodiment according to a second embodiment.

DETAILED DESCRIPTION OF THE INVENTION

Figure 3B:
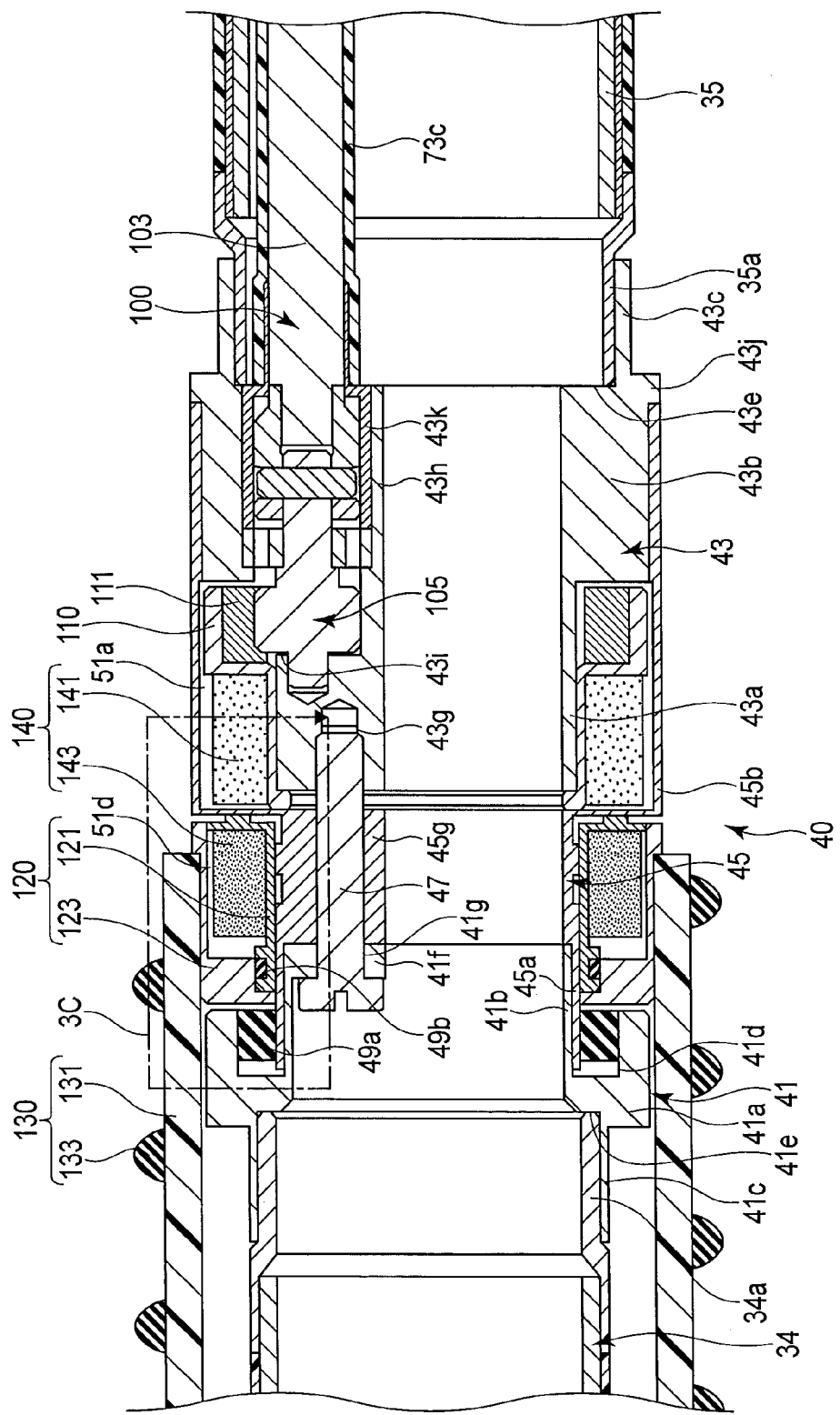
FIG. 3B is a cross-sectional view showing the coupling configuration of the proximal end portion of the passive bending portion and the distal end portion of the flexible tube portion and a configuration 2 of an endoscope.

Embodiments according to the present invention will now be described with reference to the drawings hereinafter.

[First Embodiment]

[Configuration]

A first embodiment will now be described with reference to FIG. 1, FIG. 2, FIG. 3A, FIG. 3B, FIG. 3C, FIG. 3D, FIG. 4, and FIG. 5. It is to be noted that some members are omitted in some drawings to clarify the drawings and, for example, a drive member 101 and a cable 101a are omitted in FIG. 2, and a helical rotation member 130 is omitted in FIG. 3A. Further, in the following description, a longitudinal axial C means, e.g., a longitudinal axis of an insertion unit 30. A longitudinal direction means, e.g., a longitudinal direction of the insertion unit 30. A radial direction means a radial direction of the insertion unit 30.

[Endoscopic System 10]

As shown in FIG. 1, an endoscopic system 10 has an endoscope 20 having an insertion unit 30 that is inserted into or removed from, e.g., a lumen of a subject and a control unit 200 that controls a propulsive force that aids insertion and removal (advance and retreat) when the insertion unit 30 is inserted into and removed from (advanced and retreated) the lumen. The endoscope 20 is an insertion apparatus that is inserted into a lumen and also an insertion and removal apparatus that is inserted into and removed from the lumen. The lumen means, e.g., the inside of a small intestine, the inside of a large intestine, a pylorus, a duodenum, and a cardia.

Furthermore, as shown in FIG. 1, the endoscopic system 10 further has a display portion 210 that displays images acquired by the endoscope 20 and a light source unit 220 arranged so that light can be emitted from a distal end portion of the insertion unit 30 to an observation target. Each image acquired by the endoscope 20 represents, e.g., an observation target in a lumen. The observation target is, e.g., an affected part or a lesioned part in a lumen.

[Configuration 1 of Endoscope 20]

As shown in FIG. 1, the endoscope 20 has the elongated insertion unit 30 that is inserted into or removed from a lumen and has the longitudinal axis C and an operation unit 70 that is coupled with a proximal end portion of the insertion unit 30 to operate the endoscope 20. Such an endoscope 20 can be cleaned and sterilized.

[Insertion Unit 30]

As shown in FIG. 1, the insertion unit 30 has a distal end hard portion 31, an active bending portion 33, a passive bending portion 34, and a flexible tube portion 35 from the distal end portion side of the insertion unit 30 toward the proximal end portion side of the insertion unit 30. A proximal end portion of the distal end hard portion 31 is coupled with a distal end portion of the active bending portion 33, a proximal end portion of the active bending portion 33 is coupled with a distal end portion of the passive bending portion 34, and a proximal end portion of the passive bending portion 34 is coupled with a distal end portion of the flexible tube portion 35.

The distal end portion 31 is the distal end portion of the insertion unit 30, and it is hard and does not bend. The distal end hard portion 31 has a non-illustrated imaging unit that images an observation target and a non-illustrated emitting portion from which light emits toward the observation target. The emitting portion is optically connected with the light source unit 220 and allows light led from the light source unit 220 to exit toward the observation target.

The active bending portion 33 bends in a desired direction, e.g., an up-and-down direction by an operation of a later-described bending operating portion 73a shown in FIG. 2. When the active bending portion 33 bends, a position and a direction of the distal end hard portion 31 vary, the non-illustrated observation target is illuminated with light, and the non-illustrated observation target is captured in an observation viewing field. The active bending portion 33 has, e.g., node rings that are coupled with each other so that the node rings adjacent to each other can revolve and a resin outer coat that is arranged on the outside of the node rings and covers the node rings.

The passive bending portion 34 has desirable flexibility. Therefore, the passive bending portion 34 bends by an external force. The passive bending portion 34 is a tubular member covered with a later-described helical rotation member 130. The passive bending portion 34 has, e.g., a metal helical tube, a net-like reticular tube that is arranged on the outside of the helical tube and covers the helical tube, and a resin outer coat that is arranged on the outside of this reticular tube and covers the reticular tube. Alternatively, the passive bending portion 34 may have, e.g., node rings that are coupled with each other so that the node rings adjacent to each other can revolve and a resin outer coat that is arranged on the outside of the node rings and covers the node rings. In other words, in the insertion unit 20, a portion covered with the later-described helical rotation member 130 functions as the passive bending portion 34.

The flexible tube portion 35 has desirable flexibility. Therefore, the flexible tube portion 35 bends by an external force. The flexile tube portion 35 is a tubular member extended from a later-described main body portion 71 in the operation unit 70. The flexible tube portion 35 has, e.g., a metal helical tube, a net-like reticular tube that is arranged on the outside of this helical tube and covers the helical tube, and a resin outer coat that is arranged on the outside of this reticular tube and covers the reticular tube.

As shown in FIG. 3A and FIG. 3B, the proximal end portion of the passive bending portion 34 is coupled with a bending portion side mouth ring 34a. Further, as shown in FIG. 3A and FIG. 3B, the distal end portion of the flexible tube portion 35 is coupled with a flexible tube portion side mouth ring 35a.

[Coupling Configuration 40 of Proximal End Portion of Passive Bending Portion 34 and Distal End Portion of Flexible Tube Portion 35]

As shown in FIG. 3A and FIG. 3B, a coupling configuration 40 has a cylindrical mouth ring 41 that is fitted onto the proximal end portion of the bending portion side mouth ring 34a to assure water-tightness, a cylindrical mouth ring 43 that is fitted onto the flexible tube portion side mouth ring 35a to assure water-tightness, a cylindrical member 45 that couples the mouth ring 41 with the mouth ring 43 in the longitudinal direction to assure water-tightness, and a coupling member 47 such as a pin that couples the mouth ring 41, the mouth ring 43, and the cylindrical member 45 with each other. The coupling configuration 40 can be cleaned and sterilized.

[Mouth Ring 41]

As shown in FIG. 3B, the mouth ring 41 has a distal end portion 41a that is exposed from the bending portion side mouth ring 34a and the cylindrical member 45 when the mouth ring 41 is coupled with the bending portion side mouth ring 34a and the cylindrical member 45 and a proximal end portion 41b that is inserted and fitted into a distal end portion 45a of the cylindrical member 45. The mouth ring 41 is formed into a convex shape so that the distal end portion 41a becomes thick and the proximal end portion 41b becomes thin, and the mouth ring 41 has a cylindrical shape.

Moreover, as shown in FIG. 3B, the mouth ring 41 has an annular erected portion 41a that is arranged at an edge portion of the distal end portion 41a and erected toward the passive bending portion 34 from the entire edge portion and an annular groove portion 41d that is arranged at the distal end portion 41a and concaved from the proximal end portion 41b toward the distal end portion 41a. The bending portion side mouth ring 34a is inserted and fitted into the erected portion 41c.

As shown in FIG. 3B, when the proximal end portion 41b is inserted into the distal end portion 45a of the cylindrical member 45, the distal end portion 45a is inserted into the groove portion 41d. As shown in FIG. 3B and FIG. 3C, in this state, a water-tightness assuring member 49a such as an O-ring is arranged in the groove portion 41d. The water-tightness assuring member 49a is appressed against an inner peripheral surface of the groove portion 41d, the distal end portion 41a of the mouth ring 41, and the distal end portion 45a of the cylindrical member 45 to assure water-tightness between the mouth ring 41 and the cylindrical member 45.

It is to be noted that, as shown in FIG. 3B, as seen in an outer diameter of the mouth ring 41, the erected portion 41c is larger than the proximal end portion 41b and smaller than the distal end portion 41a. Further, as seen in an inner diameter of the mouth ring 41, the distal end portion 41a is substantially equal to the proximal end portion 41b. Furthermore, as seen in the inner diameter of the mouth ring 41, the erected portion 41c is larger than the distal end portion 41a. Therefore, the mouth ring 41 has an abutting portion 41e that is a step which is arranged over the entire inner peripheral surface of the mouth ring 41 and on which the bending portion side mouth ring 34a inserted in the erected portion 41c abuts. When the bending portion side mouth ring 34a abuts on the abutting portion 41e, the abutting portion 41e prevents the bending portion side mouth ring 34a from being inserted into the proximal end portion 41b from the distal end portion 41a.

Moreover, as shown in FIG. 3B, the mouth ring 41 has a tabular protruding portion 41f that is formed by protruding part of a peripheral surface of the proximal end portion 41b toward the inside of the mouth ring 41. The protruding portion 41f has an engagement hole 41g that is penetrated in the protruding portion 41f in the longitudinal direction. The coupling member 47 penetrates through and engages with the engagement hole 41g when the proximal end portion of the passive bending portion 34 is coupled with distal end portion of the flexible tube portion 35.

[Mouth Ring 43]

As shown in FIG. 3B, the mouth ring 43 has a distal end portion 43a that is inserted into a proximal end portion 45b of the cylindrical member 45 and a proximal end portion 43b that is inserted and fitted into the proximal end portion 45b of the cylindrical member 45. The mouth ring 43 is formed into a convex shape so that the distal end portion 43a becomes thin and the proximal end portion 41b becomes thick, and the mouth ring 43 has a cylindrical shape.

Further, as shown in FIG. 3B, the mouth ring 43 has a concave portion 43g that is arranged at an edge portion of the distal end portion 43a, and is also arranged on substantially the same straight light as the engagement hole 41g in the longitudinal direction when the proximal end portion of the passive bending portion 34 is coupled with the distal end portion of the flexible tube portion 35, and engages with the coupling member 47.

Furthermore, as shown in FIG. 3B, the mouth ring 43 has an annular erected portion 43c which is arranged at an edge portion of the proximal end portion 43b and erected from the entire edge portion toward the flexible tube portion 35 and into which the flexible tube portion side mouth ring 35a is inserted and fitted. The erected portion 43c is exposed from the proximal end portion 45b of the cylindrical member 45 when the distal end portion 43a and the proximal end portion 43b are inserted into the proximal end portion 45b of the cylindrical member 45.

It is to be noted that, as shown in FIG. 3B, as seen in an outer diameter of the mouth ring 43, the erected portion 43c is larger than the distal end portion 43a and smaller than the proximal end portion 43b. Furthermore, as seen in an inner diameter of the mouth ring 43, the distal end portion 43a is substantially equal to the proximal end portion 43b in size. Moreover, as seen in the inner diameter of the mouth ring 43, the erected portion 43c is larger than the proximal end portion 43b. Therefore, the mouth ring 43 has an abutting portion 43e that is a step which is arranged over the entire inner peripheral surface of the mouth ring 43 and on which the flexible tube portion side mouth ring 35a inserted in the erected portion 43c abuts. When the flexible tube portion side mouth ring 35a abuts on the abutting portion 43e, the abutting portion 43e prevents the flexible tube portion side mouth ring 35a from being inserted into the distal end portion 41a from the proximal end portion 43b.

Moreover, as shown in FIG. 3B, the mouth ring 43 has a concave portion 43h which is concaved from the edge portion of the proximal end portion 43b toward the distal end portion 43a and in which a later-described gear member 105 is arranged and an opening portion 43i which is arranged in part of an outer peripheral surface of the distal end portion 43a and communicates with the outside and the concave portion 43h in the circumferential direction of the mouth ring 43. The opening portion 43i is arranged in such a manner that the gear member 105 arranged in the concave portion 43h protrudes toward the outside from the opening portion 43i. The inside of the mouth ring 43 including the concave portion 43h and the opening portion 43i corresponds to the inside of the insertion unit 30.

Additionally, as shown in FIG. 3B, the mouth ring 43 has a preventing portion 43j that prevents the proximal end portion 45b of the cylindrical member 45 from being inserted to the flexible tube portion 35 side from the proximal end portion 43b. The preventing portion 43j is a protruding portion that protrudes from an outer peripheral surface of the proximal end portion 43b toward the outside. The preventing portion 43j is arranged on the outer peripheral surface of the mouth ring 43 over the entire circumference of the mouth ring 43 in the circumferential direction of the mouth ring 43 and abuts on the proximal end portion 45b of the cylindrical member 45 in the longitudinal direction.

[Cylindrical Member 45]

As shown in FIG. 3B, the cylindrical member 45 has a distal end portion 45a that is fitted to the distal end portion 41a of the mouth ring 41 and a proximal end portion 45b that is fitted to the proximal end portion 43b of the mouth ring 43 while covering the distal end portion 43a of the mouth ring 43. The cylindrical member 45 is formed into a convex shape so that the distal end portion 45 becomes thin and the proximal end portion 45b becomes thick, and the cylindrical member 45 has a cylindrical shape.

Further, as shown in FIG. 3B, the cylindrical member 45 has a holding portion 45g that is arranged on an inner peripheral surface of the distal end portion 45a to be integral with the inner peripheral surface of the distal end portion 45a and holds the coupling member 47. The holding portion 45g is arranged on substantially the same straight line as the engagement hole 41g and the concave portion 43g in the longitudinal direction when the proximal end portion of the passive bending portion 34 is coupled with the distal end portion of the flexible tube portion 35. The holding portion 45g holds the coupling member 47 when the coupling member 47 penetrates through the holding portion 45g.

As shown in FIG. 3B and FIG. 3C, the proximal end portion 45b covers the distal end portion 43a of the mouth ring 43 and it is fitted to the proximal end portion 43b of the mouth ring 43 when it is inserted into the mouth ring 43. When the proximal end portion 45b covers the distal end portion 43a of the mouth ring 43, a ring-shaped hermetically sealed space portion 51a is formed between the proximal end portion 45b and the distal end portion 43a in the radial direction. Watertightness is assured for the space portion 51a. Since a later-described first magnetic force generating portion 141 is arranged in the space portion 51a, the cylindrical member 45 functions as a cover that covers the first magnetic force generating portion 141. This space portion 51a communicates with an opening portion 43i. The inside of the cylindrical member 45 including the space portion 51a represents the inside of the insertion unit 30. The outside of the cylindrical member 45 represents the outside of the insertion unit 30.

It is to be noted that, in regard to an outer diameter of the cylindrical member 45, an outer diameter of the proximal end portion 45b is substantially equal to an outer diameter of the distal end portion 41a of the mouth ring 41 and an outer diameter of the preventing portion 43j of the mouth ring 43.

Furthermore, as shown in FIG. 3C, the cylindrical member 45 has protruding portions 45k that are arranged on the outer peripheral surface of the distal end portion 45a and protrude from the outer peripheral surface toward the outside in the radial direction of the cylindrical member 45. The protruding portions 45k are apart from each other at desired intervals in the longitudinal direction in FIG. 3C and also apart from each other at desired intervals in the radial direction of the cylindrical member 45 as shown in FIG. 3D, for example.

[Example of Coupling of Proximal End Portion of Passive Bending Portion 34 and Distal End Portion of Flexible Tube Portion 35]

(Step 1)

The flexible tube portion side mouth ring 35a is inserted into and fitted to the erected portion 43c of the mouth ring 43.

At this time, when the flexible tube portion side mouth ring 35a abuts on the abutting portion 43e, it is prevented from being inserted into the distal end portion 43a from the proximal end portion 43b of the mouth ring 43.

(Step 2)

Then, the mouth ring 43 is inserted into the proximal end portion 45b of the cylindrical member 45 so that the concave portion 43g and the holding portion 45g can be arranged on substantially the same straight line in the longitudinal direction. At this time, the distal end portion 43a of the mouth ring 43 is covered with the proximal end portion 45b of the cylindrical member 45, and the proximal end portion 43b of the mouth ring 43 is fitted to the proximal end portion 45b of the cylindrical member 45. As a result, the hermetically sealed water-tight space portion 51a is formed.

When the mouth ring 43 is fitted to the cylindrical member 45, the mouth ring 43 and the cylindrical member 45 assure water-tightness.

When the proximal end portion 45b abuts on the preventing portion 43j, the cylindrical member 45 is prevented from being inserted into the flexible tube portion 35 side from the proximal end portion 43b of the mouth ring 43.

(Step 3)

Then, the proximal end portion 41b of the mouth ring 41 is inserted into and fitted to the distal end portion 45a of the cylindrical member 45 so that the engagement hole 41g and the concave portion 43g can be arranged on substantially the same straight line in the longitudinal direction.

The water-tightness assuring member 49a is arranged in the groove portion 41d and appressed against the distal end portion 41a of the mouth ring 41 and the distal end portion 45a of the cylindrical member 45. As a result, the water-tightness assuring member 49a assures water-tightness between the mouth ring 41 and the cylindrical member 45.

(Step 4)

Then, the coupling member 47 penetrates through the engagement hole 41g and the holding portion 45g and engages with the concave portion 43g. As a result, the flexible tube portion 35, the mouth ring 43, the cylindrical member 45, and the mouth ring 41 are coupled with each other.

(Step 5)

Moreover, the bending portion side mouth ring 34a is inserted into and fitted to the erected portion 41c of the mouth ring 41. As a result, the proximal end portion of the passive bending portion 34 is coupled with the distal end portion of the flexible tube portion 35.

At this time, when the bending portion side mouth ring 34a abuts on the abutting portion 41e, it is prevented from being inserted into the proximal end portion 41b from the distal end portion 41a.

[Operation Unit 70]

As shown in FIG. 1, the operation unit 70 has the main body portion 71 to which the flexible tube portion 35 is extended, a grip portion 73 that is coupled with a proximal end portion of the main body portion 71 and gripped by an operator who operates the endoscope 20, and a universal cord 75 connected with the grip portion 73.

As shown in FIG. 1 and FIG. 2, the grip portion 73 has a bending operating portion 73a that bends the active bending portion 33, a drive member insertion opening 73b into which a later-described drive member 101 is inserted, and a rotation operating portion 73d that operates a rotating direction of a later-described shaft member 103.

The bending operating portion 73a is connected with a proximal end portion of a non-illustrated operation wire. The operation wire is inserted into the grip portion 73, the main body portion 71, and the flexible tube portion 35. Further, a distal end portion of the operation wire is coupled with the distal end portion of the active bending portion 33. When the bending operating portion 73a is operated and the operation wire is pulled, the active bending portion 33 is bent.

As shown in FIG. 1, the drive member insertion opening 73b is coupled with a proximal end portion of a shaft member insertion channel 73c. The drive member insertion opening 73b is an insertion opening through which the shaft member 103 is inserted into the shaft member insertion channel 73c. As shown in FIG. 1 and FIG. 3B, the shaft member insertion channel 73c is arranged to extend from the grip portion 73 to the flexible tube portion 35 via the main body portion 71 in inside of the insertion unit 30. Further, a distal end portion of the shaft member insertion channel 73c communicates with a concave portion 43h. In detail, as shown in FIG. 3B, the distal end portion of the shaft member insertion channel 73c is arranged in the concave portion 43h, and it is coupled with a cylindrical member 43k protruding into the flexible tube portion side mouth ring 35a.

As shown in FIG. 1 and FIG. 2, the rotation operating portion 73d has a counterclockwise operating portion 73e that operates the shaft member 103 so that the later-described shaft member 103 can rotate counterclockwise by a drive force of the drive member 101 and a clockwise operating portion 73f that operates the shaft member 103 so that the later-described shaft member 103 can rotate clockwise by the drive force of the driving member 101. The counterclockwise operating portion 73e and the clockwise operating portion 73f are connected to the control unit 200 through the universal cord 75 and a connecting portion 75a.

The universal cord 75 has a connecting portion 75a that is connected to the control unit 200 and the light source unit 220.

[Configuration 2 of Endoscope 20]

As shown in FIG. 1, FIG. 3B, and FIG. 3C, the endoscope 20 further has a rotation drive mechanism 100, a first rotation member 110, a second rotation member 120, a helical rotation member 130, and a magnetic force generation mechanism 140. The rotation drive mechanism 100, the first rotation member 110, the second rotation member 120, the helical rotation member 130, and the magnetic force generation mechanism 140 are an auxiliary propulsion mechanism that provides the insertion unit 30 with propulsive force for inserting or removing the insertion unit 30 into or from a lumen and aids propulsion of the insertion unit 30. Furthermore, the rotation drive mechanism 100, the first rotation member 110, the second rotation member 120, the helical rotation member 130, and the magnetic force generation mechanism 140 are also an auxiliary insertion and removal mechanism that aids insertion and removal of the insertion unit 30 into or from a lumen.

[Rotation Drive Mechanism 100]

As shown in FIG. 1 and FIG. 3B, the rotation drive mechanism 100 is arranged inside the insertion unit 30. As shown in FIG. 1 and FIG. 3B, the rotation drive mechanism 100 has a drive member 101 that is connected to the control unit 200 through a cable 101a and inserted into the drive member insertion opening 73b, a shaft member 103 that has a distal end portion and a proximal end portion coupled with the drive member 101 and rotates around the longitudinal axis C of the insertion unit 30 by drive force of the drive member 101, and a gear member 105 which is an outer peripheral tooth portion arranged at the distal end portion of the shaft member 103.

The drive member 101 is, e.g., a motor. The drive member 101 has a drive force that rotates the first rotation member 110.

As shown in FIG. 3B, the shaft member 103 is inserted into the shaft member insertion channel 73c. The shaft member 103 is, e.g., a torque wire having flexibility.

The gear member 105 is arranged at the distal end portion of the shaft member 103 so that it can rotate in accordance with rotation of the shaft member 103. Moreover, the gear member 105 is arranged in the concave portion 43h while being arranged at the distal end portion of the shaft member 103. The gear member 105 is pivotally supported in the concave portion 43h so that it can rotate. The gear member 105 is exposed to the outside from the opening portion 43i to mesh with the first rotation member 110. When the gear member 105 rotates in accordance with rotation of the shaft member 103 while meshing with the first rotation member 110, it rotates the first rotation member 110.

The shaft member 103 and the gear member 105 are a transmitting rotation member that transmits drive force of the drive member 101 to the first rotation member 110 and rotates the first rotation member 110 by the drive force.

[First Rotation Member 110]

As shown in FIG. 3B, the first rotation member 110 is, e.g., a gear base member. The first rotation member 110 has, e.g., a cylindrical shape. It is to be noted that the first rotation member 110 may have an elliptic tubular shape as long as it is a tubular shape, and the shape is not restricted in particular. The first rotation member 110 has an inner peripheral tooth portion 111 that is fixed on an inner peripheral surface of the first rotation member 110 and meshes with the gear member 105. This inner peripheral tooth portion 111 has a ring-like shape. The first rotation member 110 is fitted to the distal end portion 43a in such a manner that the inner peripheral tooth portion 111 meshes with the gear member 105, the first rotation member 110 is placed in the space portion 51a, and the first rotation member 110 is covered with the proximal end portion 45b of the cylindrical member 45. In this manner, the first rotation member 110 is arranged inside the inserting portion 30.

When the gear member 105 rotates around the longitudinal axis C while meshing with the inner peripheral tooth portion 111, the first rotation member 110 rotates around the longitudinal axis C together with the inner peripheral tooth portion 111. As described above, the first rotation member 110 is coupled with the rotation drive mechanism 100 and rotated around the longitudinal axis C by the rotation drive mechanism 100.

[Second Rotation Member 120]

As shown in FIG. 3B, the second rotation member 120 is, e.g., a rotation base member. The second rotation member 120 has a cylindrical shape. It is to be noted that the second rotation member 120 may have an elliptic tubular shape as long as it is a tubular shape, and the shape is not restricted in particular. The second rotation member 120 is attached to the outer peripheral surface of the insertion unit 30 when it is inserted into the distal end portion 45a of the cylindrical member 45. At this time, the second rotation member 120 is attached to the outer peripheral surface of the insertion unit 30 in such a manner that the second rotation member 120 is adjacent to the first rotation member 110 in the longitudinal direction and a central axis of the first rotation member 110 and a central axis of the second rotation member 120 are substantially coaxially arranged each other. At the same time, the second rotation member 120 is arranged in such a manner that the second rotation member 120 can rotate around the longitudinal axis C with respect to the insertion unit 30 including the cylindrical member 45. In other words, the second rotation member 120 slides around the longitudinal axis C relative to the cylindrical member 45 in such a manner that it rotates.

As shown in FIG. 3C, the second rotation member 120 is formed when a ring-like inner base member 121 is combined with a ring-like outer base member 123. The inner base member 121 is narrower than the outer base member 123, inserted into the outer base member 123, and fitted to the outer base member 123 to assure water-tightness.

As shown in FIG. 3C, the inner base member 122 is inserted to the distal end portion 45a side of the cylindrical member 45 so that a planar inner peripheral surface of the inner base member 121 faces the cylindrical member 45 in the radial direction and abuts on the protruding portion 45k. Therefore, when the inner base member 121 is inserted into the distal end portion 45a of the cylindrical member 45, a space portion 51b communicating with the outside is formed between the second rotation member 120 (the inner base member 121) and the insertion unit 30 (the distal end portion 45a, the protruding portion 45k of the cylindrical member 45). The space portion 51b is arranged for, e.g., cleaning and sterilization of the insertion unit 30 having the second rotation member 130 attached thereto.

Figure 4:
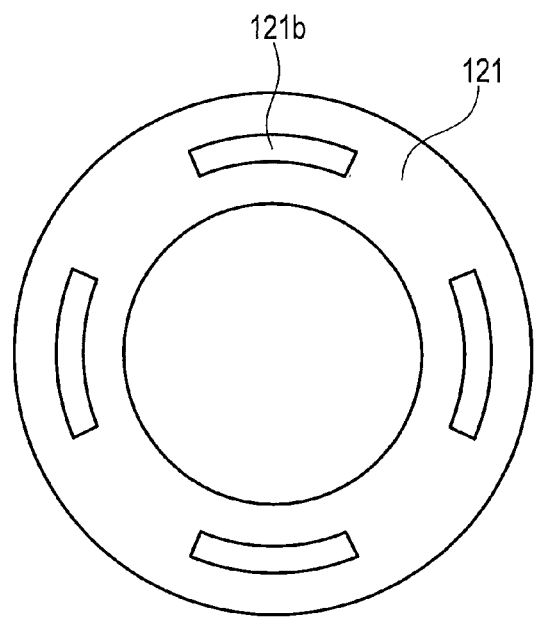
FIG. 4 is a front view of an inner base member seen from a protruding portion side.

Additionally, as shown in FIG. 3C, an edge portion of the inner base member 121 arranged on the proximal end portion 45b side of the cylindrical member 45 is bent outward. This edge portion is formed as a planar outer flange portion arranged over the entire circumference of the inner base member 121 along the circumferential direction of the inner base member 121. The edge portion has protruding portions 121b protruding from the edge portion of the inner base member 121 toward a flat surface portion 45m of the cylindrical member 45 in the longitudinal direction. The flat surface portion 45m of the cylindrical member 45 corresponds to a portion that is bent from the distal end portion 45a toward the proximal end portion 45b in the distal end portion 45a formed into a convex shape. The flat surface portion 45m is arranged to be orthogonal to the longitudinal axis C. As shown in FIG. 4, the protruding portions 121b are apart from each other at desired intervals in the circumferential direction of the inner base member 121. The protruding portions 121b have substantially the same shapes, substantially the same thicknesses, and substantially the same lengths in the circumferential direction of the inner base member 121.

As shown in FIG. 3C, when the inner base member 121 is inserted to the distal end portion 45a of the cylindrical member 45, the edge portion of the inner base member 121 faces the flat surface portion 45m of the cylindrical member 45 in the longitudinal direction and further the protruding portions 121b abuts on the edge portion of the cylindrical member 45 in the longitudinal direction. As a result, a space portion 51c communicating with the outside is formed between the second rotation member 120 (the inner base portion 121, the protruding portions 121b) and the insertion unit 30 (the edge portion of the cylindrical member 45) in the longitudinal direction. The space portion 51c communicates with the space portion 51b. The space portion 51c is arranged for, e.g., cleaning and sterilization of the insertion unit 30 having the second rotation member 120 attached thereto.

An outer diameter of the outer base member 123 is substantially the same as an outer diameter of the proximal end portion 45b of the cylindrical member 45.

As shown in FIG. 3C, in the outer base member 123, an edge portion 123a of the outer base member 123 arranged on the distal end portion 41a side of the mouth ring 41 is bent inward. The edge portion 123a is formed as an inner flange portion arranged over the entire circumference of the outer base member 123 along the circumferential direction of the outer base member 123. The edge portion 123a is arranged to cover the groove portion 41d and prevents the water-tightness assuring member 49a from coming off the groove portion 41d. Further, the edge portion 123a is fitted to the edge portion of the inner base member 121 arranged on the distal end portion 41a side of the mouth ring 41 to assure water-tightness. Therefore, a water-tightness assuring member 49b such as an O-ring is arranged between the edge portion 123a and the edge portion of the inner base member 121.

As shown in FIG. 3C, the inner baser member 121 is inserted into the outer base member 123 in such a manner that a hermetically sealed ring-shaped space portion 51d is formed between the inner base member 121 and the outer base member 123 in the radial direction and both end portions of the inner base member 121 abut on both end portions of the outer flange portion. Water-tightness is assured for the space portion 51d.

As shown in FIG. 3B and FIG. 3C, according to this embodiment, in this state, the second rotation member 120 is interposed between the distal end portion 41a of the mouth ring 41 and the proximal end portion 45b of the cylindrical member 45 so that the second rotation member 120 can rotate around the longitudinal axis C with respect to the insertion unit 30. In other words, the second rotation member 120 is embedded in a groove portion 37 that is formed from the outer peripheral surface toward the inner peripheral surface of the insertion unit 30 and arranged on the outer peripheral surface of the insertion unit 30 over the entire circumference of the insertion unit 30 along the periaxial direction of the insertion unit 30. As a result, the second rotation member 120 is prevented from coming off the insertion unit 30. It is to be noted that the groove portion 37 means a space portion formed between the distal end portion 41a of the mouth ring 41 and the proximal end portion 45b of the cylindrical member 45 in the longitudinal direction. Furthermore, the groove portion 37 may be arranged to be adjacent to the space portion 51a in the longitudinal direction.

At this time, as shown in FIG. 3C, the space portion 51d is arranged on substantially the same straight line as the space portion 51a in the longitudinal direction, the space portion 51d is adjacent to the space portion 51a, and a central axis of the space portion 51d and a central axis of the space portion 51a are arranged on substantially the same straight line. Further, the protruding portions 121b abut on the flat surface portion 45m of the cylindrical member 45, the planar inner peripheral surface of the inner base member 121 abuts on the protruding portions 45k, and the edge portion of the outer base member 123 prevents the water-tightness assuring member 49a from coming off the groove portion 41d. As a result, the second rotation member 120 is positioned in the longitudinal direction.

[Helical Rotation Member 130]

As shown in FIG. 1 and FIG. 3B, the helical rotation member 130 has a cylindrical main body portion 131 into which the insertion unit 30 can be inserted and which is fixed to the second rotation member 120 and can rotate around the longitudinal axis C with rotation of the second rotation member and a fin portion 133 which is arranged on an outer peripheral surface of the main body portion 131 and also helically arranged around the longitudinal axis C. Such a helical rotation member 130 is attached to the insertion unit 30 of the endoscope 20 and can be inserted into a lumen. In detail, a proximal end portion of the main body portion 131 may be detachably fixed to the second rotation member 120 or may be integrally formed with the second rotation member 120. When the proximal end portion of the main body portion 131 is integrally fixed with the second rotation member 120, the insertion unit 30 is inserted in the helical rotation member 130 and the second rotation member 120, and the second rotation member 120 is attached to the insertion unit 30.

The main body portion 131 is made of, e.g., a cleanable and sterilizable resin. The main body portion 131 has flexibility. This resin is, e.g., polyurethane. A distal end portion of the main body portion 131 is secured to, e.g., the passive bending portion 34. The proximal end portion of the main body portion 131 is secured to the outer peripheral surface of the outer base member 123. As described above, the second rotation member 120 including the outer base member 123 is also an attaching portion that attaches the helical rotation member 130 to the insertion unit 30. It is to be noted that the main body portion 131 may have, e.g., an elliptic tubular shape as long as it is a tubular shape, and the shape is not restricted in particular.

The fin portion 133 is made of, e.g., cleanable and sterilizable rubber. The fin portion 133 is fixed to an outer peripheral surface of the main body portion 131 by, e.g., bonding or welding. As shown in FIG. 1, in a direction to see the distal end portion from the proximal end portion of the main body portion 131, the fin portion 133 is helically arranged clockwise, for example. As shown in FIG. 1, a distal end portion of the fin portion 133 is arranged at the distal end portion of the main body portion 131, and a proximal end portion of the fin portion 133 is arranged at the proximal end portion of the main body portion 131.

When the insertion unit 30 is inserted into a lumen, the fin portion 133 abuts on an inner wall of the lumen. In this state, when the main body portion 131 rotates around the longitudinal axis C, the fin portion 133 engages with the inner wall of the lumen, and a propulsive force acts on the insertion unit 30 in the longitudinal direction. As a result, the insertion unit 30 moves forward and backward (inserted and removed) in the lumen. The propulsive force means an insertion force which acts on the insertion unit 30 in the inserting direction of the insertion unit 30 and aids insertion of the insertion unit 30 or a removal force which acts on the insertion unit 30 in a removing direction of the insertion unit 30 and aids removal of the insertion unit 30.

When the main body portion 131 rotates in the clockwise direction, the insertion force acts on the insertion unit 30, and insertion properties of the insertion unit 30 are improved. Further, when the main body portion 131 rotates in the counterclockwise direction, the removal force acts on the insertion unit 30, and removal properties of the insertion unit 30 are improved.

[Magnetic Force Generation Mechanism 140]

As shown in FIG. 3B and FIG. 3C, the magnetic force generation mechanism 140 has a ring-shaped first magnetic force generating portion 141 arranged on the first rotation member 110 and a ring-shaped second magnetic force generating portion arranged on the second rotation member 120. The first magnetic force generating portion 141 and the second magnetic force generating portion 143 are, e.g., magnets, and they have substantially the same sizes.

Figure 5:
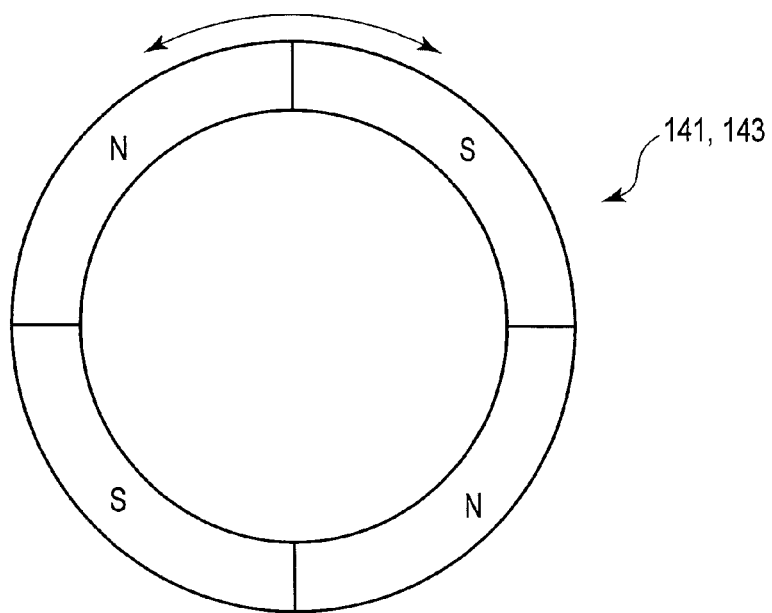
FIG. 5 is a view showing a configuration of a first magnetic force generating portion and a configuration of a second magnetic force generating portion.

As shown in FIG. 5, the first magnetic force generating portion 141 is formed by alternately arranging magnets having the N pole and magnets having the S pole in the circumferential direction of the first magnetic force generating portion 141. The magnets having the N pole and the magnets having the S pole, which are equal in number, are arranged, and they have substantially the same sizes.

As shown in FIG. 5, the second magnetic force generating portion 143 is formed by alternately arranging magnets having the N pole and magnets having the S pole in the circumferential direction of the second magnetic force generating portion 143. The magnets having the N pole and the magnets having the S pole, which are equal in number, are arranged, and they have substantially the same sizes.

A configuration of the first magnetic force generating portion 141 is substantially the same as a configuration of the second magnetic force generating portion 143. Therefore, for example, the magnets having the N pole in the first magnetic force generating portion 141 are arranged to be equal in number with the magnets having the N pole in the second magnetic force generating portion 143 and the magnets having the S pole in the second magnetic force generating portion 143, and they have substantially the same sizes. Further, for example, the magnets having the S pole in the first magnetic force generating portion 141 are arranged to be equal in number with the magnets having the N pole in the second magnetic force generating portion 143 and the magnets having the S pole in the second magnetic force generating portion 143, and they have substantially the same sizes. It is to be noted that, in each of the first magnetic force generating portion 141 and the second magnetic force generating portion 143, arranging at least one magnet having the N pole and at least one magnet having the S pole can suffice.

As shown in FIG. 3B and FIG. 3C, the first magnetic force generating portion 141 is inserted into the first rotation member 110 and fitted to the first rotation member 110 in such a manner that the first magnetic force generating portion 141 is placed in the hermetically sealed space portion 51a, the first magnetic force generating portion 141 is adjacent to the space portion 51d in the longitudinal direction, and the first magnetic force generating portion 141 is covered with the proximal end portion 45b of the cylindrical member 45. In this manner, the first magnetic force generating portion 141 is arranged inside the insertion unit 30 and annularly arranged at a cylindrical end portion of the first rotation member 110. This end portion means, e.g., the flat surface portion 45m of the cylindrical member 45 on which the protruding portions 121b abut. Furthermore, this end portion corresponds to a shape of the first rotation member 110, and it has, e.g., a tubular shape if the first rotation member 110 has, e.g., a tubular shape. It is to be noted that the first magnetic force generating portion 141 is covered with the proximal end portion 45b of the cylindrical member 45 and placed in the space portion 51a, and hence water-tightness is assured with respect to the outside.

As shown in FIG. 3B and FIG. 3C, since the first magnetic force generating portion 141 is fitted to the first rotation member 110, when the first rotation member 110 rotates around the longitudinal axis C, the first magnetic force generating portion 141 rotates around the longitudinal axis C together with the first rotation member 110.

As shown in FIG. 3B and FIG. 3C, the second magnetic force generating portion 143 is inserted into the inner base member 121 and fitted to the inner base member 121 in such a manner that the second magnetic force generating portion 143 is placed in the hermetically sealed space portion 51d, the second magnetic force generating portion 143 is adjacent to the first magnetic force generating portion 141 in the longitudinal direction, and the second magnetic force generating portion 143 is covered with the outer base member 123. As described above, the second magnetic force generating portion 143 is arranged on the outside of the insertion unit 30 and annularly arranged at the cylindrical end portion of the second rotation member 120. This end portion corresponds to a planar edge portion of the inner base member 121 at which the protruding portions 121b are arranged. The cylindrical end portion of the second rotation member 120 is adjacent to the cylindrical end portion of the first rotation member 110 in the longitudinal direction.

Furthermore, this end portion corresponds to a shape of the second rotation member 120, and it has, e.g., a tubular shape if the second rotation member 120 is formed into, e.g., a tubular shape. It is to be noted that the second magnetic force generating portion 143 is covered with the outer base member 123 and placed in the space portion 51d, and hence water-tightness is assured with respect to the outside.

As shown in FIG. 3B and FIG. 3C, the space portion 51d is arranged on substantially the same straight line as the space portion 51a in the longitudinal direction, the space portion 51d is adjacent to the space portion 51a in the longitudinal direction, and the central axis of the space portion 51d and the central axis of the space portion 51a are arranged on substantially the same straight line. Therefore, when the second magnetic force generating portion 143 is arranged in the space portion 51d and the first magnetic force generating portion 141 is arranged in the space portion 51a, a distal end surface of the first magnetic force generating portion 141 is adjacent to a proximal end surface of the second magnetic force generating portion 143. Moreover, the second magnetic force generating portion 143 is arranged to be adjacent to the first magnetic force generating portion 141 so that it is laminated on the first magnetic force generating portion 141 in the longitudinal direction. At the same time, the central axis of the second magnetic force generating portion 143 is substantially coaxially arranged with the central axis of the first rotation member 110.

In this embodiment, as described above, the first magnetic force generating portion 141 and the second magnetic force generating portion 143 are arranged to be adjacent to each other in the longitudinal direction so that their magnetic forces can act each other. Therefore, when the N pole of the first magnetic force generating portion 141 is adjacent to the S pole of the second magnetic force generating portion 143 and the S pole of the first magnetic force generating portion 141 is adjacent to the N pole of the second magnetic force generating portion 143, the first magnetic force generating portion 141 and the second magnetic force generating portion 143 generate magnetic forces that enable the first rotation member 110 and the second rotation member 120 to be attracted and coupled with each other in the longitudinal direction with use of the magnetic forces.

Further, when the first rotation member 110 including the first magnetic force generating portion 141 rotates, since the magnetic force of the first magnetic force generating portion 141 and the magnetic force of the second magnetic force generating portion 143 attract and repel each other, the second rotation member 120 including the second magnetic force 143 rotates in accordance with rotation of the first rotation member 110. In other words, when the first rotation member 110 including the first magnetic force generating portion 141 rotates in a state that the first rotation member 110 and the second rotation member 120 attract each other, the first magnetic force generating portion 141 and the second magnetic force generating portion 143 generate magnetic forces that enable the second rotation member 120 to rotate in accordance with the rotation of the first rotation member 110.

Here, there is a limit in magnetic force that enables the second rotation member 120 to rotate in accordance with the rotation of the first rotation member 110. Therefore, in a case that resistance that is beyond the assumed range is produced to the helical rotation member 130 when the insertion unit 30 moves forward and backward in a lumen or that a drive force that is beyond the assumed range is transmitted to the rotation drive mechanism 100, both the first magnetic force generating portion 141 and the second magnetic force generating portion 143 function as torque limiters, and the first rotation member 110 rotates idle with respect to the second rotation member 120.

As described above, the magnetic force generation mechanism 140 is arranged in each of the first rotation member 110 and the second rotation member 120. Further, the magnetic force generation mechanism 140 generates a magnetic force that enables the first rotation member 110 and the second rotation member 120 to be attracted to and coupled with each other and a magnetic force that enables the second rotation member 120 to rotate in accordance with rotation of the first rotation member 110 when the first rotation member 110 rotates in a state that the first rotation member 110 and the second rotation member 120 are attracted to each other. Therefore, in this embodiment, the magnetic force generation mechanism 140 is arranged in the ring-like form at each of the cylindrical end portion of the first rotation member 110 and the cylindrical end portion of the second rotation member 120 that is adjacent to the end portion of the first rotation member 110. One of the end portions is associated with the shape of the first rotation member 110, and it has, e.g., a tubular shape if the first rotation member 110 is formed into, e.g., a tubular shape. Furthermore, the other end portion is associated with the shape of the second rotation member 120, and it has, e.g., a tubular shape if the second rotation member 120 is formed into, e.g., a tubular shape.

[Example of Arrangement of Rotation Drive Mechanism 100, First Rotation Member 110, Second Rotation Member 120, Helical Rotation Member 130, and Magnetic Force Generation Mechanism 140]

The arrangement of these members will be briefly described with reference to Steps 1, 2, 3, and 4 concerning the coupling of the proximal end portion of the passive bending portion 34 and the distal end portion of the flexible tube portion 35.

(Step 1)

At Step 1, in the mouth ring 43, the gear member 105 is previously arranged in the concave portion 43h to be exposed to the outside from the opening portion 43i. Moreover, on the flexible tube portion 35 side, the drive member 101 is previously inserted into the drive member insertion opening 73b so that the shaft member 103 can be inserted into the shaft member insertion channel 73c. Additionally, the flexible tube portion side mouth ring 35a is inserted into and fitted to the erected portion 43c of the mouth ring 43 so that the gear member 105 can be coupled with the shaft member 103.

(Step 2)

At Step 2, before the mouth ring 43 is fitted to the cylindrical member 45, the first rotation member 110 including the first magnetic force generating portion 141 is fitted to the distal end portion 43a of the mouth ring 43 so that the inner peripheral tooth portion 111 can mesh with the gear member 105. It is to be noted that the first magnetic force generating portion 141 may be arranged with respect to the first rotation member 110 after the first rotation member 110 is fitted to the distal end portion 43a of the mouth ring 43.

Further, when the mouth ring 43 is covered with the cylindrical member 45, the first rotation member 110 including the first magnetic force generating portion 141 is placed in the space portion 51a and covered with the proximal end portion 45b of the cylindrical member 45. In this manner, the first rotation member 110 including the first magnetic force generating portion 141 is arranged inside the insertion unit 30.

(Step 3)

At Step 3, before the mouth ring 41 is fitted to the cylindrical member 45, the second rotation member 120 including the second magnetic force generating portion 143 is inserted into the distal end portion 45a of the cylindrical member 45. As a result, the second rotation member 120 including the second magnetic force generating portion 143 is arranged outside the insertion unit 30.

When the mouth ring 41 is fitted to the distal end portion 45a of the cylindrical member 45, the second rotation member 120 including the second magnetic force generating portion 143 is interposed between the distal end portion 41a of the mouth ring 41 and the proximal end portion 45b of the cylindrical member 45 so that it can be adjacent to the first rotation member 110 including the first magnetic force generating portion 141.

The helical rotation member 130 may be previously fixed to the second rotation member 120 at Step 3 or may be fixed to the second rotation member 120 at Step 3 or subsequent steps.

[Control Unit 200]

As shown in FIG. 1, the control unit 200 has a control portion 201 which controls driving of the drive member 101 and a display portion 210 and a rotation speed input portion 203 which inputs a rotation speed of the drive member 101, especially the helical rotation member 130.

The control portion 201 controls a rotating direction of the drive member 101 in accordance with an operation of the counterclockwise operating portion 73e or the clockwise operating portion 73f. Furthermore, the control portion 201 controls a rotation speed of the drive member 101 and also controls a rotation speed of the helical rotation member 130 in accordance with an input amount of the rotation speed input portion 203.

[Function]

In a state that the first rotation member 110 and the second rotation member 120 are attracted to each other in the longitudinal direction by the first magnetic force generating portion 141 and the second magnetic force generating portion 143, the insertion unit 30 is inserted into, e.g., a lumen from a mouth. At this time, the fin portion 133 abuts on an inner wall of the lumen.

When the clockwise operating portion 73f and the rotation speed input portion 203 are operated, the control portion 201 controls a rotating direction of the drive member 101 so that the drive member 101 can rotate clockwise, and it also controls a rotating speed of the drive member 101 based on an input amount of the rotating speed input portion 203.

Furthermore, the shaft member 103 coupled with the drive member 101 and the gear member 105 arranged at the distal end portion of the shaft member 103 rotate clockwise around the longitudinal axis C. Thus, the first rotation member 110 having the inner peripheral tooth portion 111 that meshes with the gear member 105 and the first magnetic force generating portion 141 fitted to the first rotation member 110 rotate clockwise around the longitudinal axis C.

When the first magnetic force generating portion 141 rotates, the magnetic force of the first magnetic force generating portion 141 and the magnetic force of the second magnetic force generating portion 143 attract and repel each other. As a result, the second rotation member 120 including the second magnetic force generating portion 143 rotates in accordance with rotation of the first rotation member 110. Therefore, the second rotation member 120 rotates clockwise like the first rotation member 110.

Moreover, the helical rotation member 130 fixed to the second rotation member 120 rotates clockwise, the fin portion 133 engages with the inner wall of the lumen, and a propulsive force acts on the insertion unit 30 in the inserting direction of the insertion unit 30. Additionally, insertion of the insertion unit 30 is aided by the propulsive force.

It is to be noted that, when the insertion unit 30 is removed from, e.g., the lumen, the counterclockwise operating portion 73e is operated. As a result, the shaft member 103, the gear member 105, the first rotation member 110, the first magnetic force generating portion 141, the second magnetic force generating portion 143, the second rotation member 120, and the helical rotation member 130 rotate counterclockwise. Further, the propulsive acts on the insertion unit 30 in the removing direction of the insertion unit 30, and the removal of the insertion unit 30 is aided by the propulsive force.

In this embodiment, the first magnetic force generating portion 141 and the second magnetic force generating portion 143 have substantially the same configurations. Furthermore, the first magnetic force generating portion 141 is arranged at the cylindrical end portion of the first rotation member 110, and the second magnetic force generating portion 143 is arranged at the cylindrical end portion of the second rotation member 120 adjacent to the end portion of the first rotation member 110. Moreover, the first magnetic force generating portion 141 and the second magnetic force generating portion 143 are arranged to be adjacent to each other and laminated each other in the longitudinal direction.

As a result, the magnetic force of the first magnetic force generating portion 141 and the magnetic force of the second magnetic force generating portion 143 assuredly act each other. Therefore, even if the gathered inner wall tries to stretch and resistance is produced with respect to the fin portion 133, when the first magnetic force generating portion 141 rotates, the second rotation member 120 including the second magnetic force generating portion 143 assuredly rotates in accordance with the rotation of the first rotation member 110. Further, the helical rotation member 130 fixed to the second rotation member 120 assuredly rotates. The non-rotation of the helical rotation member 130 including the second rotation member 120 caused due to the resistance described above can be avoided. That is, even if the resistance is produced with respect to the helical rotation member 130 when the insertion unit 30 moves forward or backward in the lumen, the helical rotation member 130 assuredly rotates.

[Effect]

As described above, in this embodiment, the non-rotation of the helical rotation member 130 including the second rotation member 120 due to the resistance of the inner wall can be avoided by the arrangement position of the first magnetic force generating portion 141 and the second magnetic force generating portion 143. Furthermore, in this embodiment, even if the resistance of the inner wall is produced with respect to the helical rotation member 130 when the insertion unit 30 moves forward and backward in a lumen, the helical rotation member 130 can be assuredly rotated. As a result, in this embodiment, when the insertion unit 30 is inserted into or removed from the lumen, propulsion of the insertion unit 30 can be assuredly aided at the time of inserting or removing the insertion unit 30 into or from the lumen.

Moreover, in this embodiment, the first magnetic force generating portion 141 is arranged to be adjacent to the second magnetic force generating portion 143 in the longitudinal direction and laminated on the same. Additionally, the central axis of the first magnetic force generating portion 141 is substantially coaxially arranged with the central axis of the second magnetic force generating portion 143. As a result, in this embodiment, the magnetic force of the first magnetic force generating portion 141 and the magnetic force of the second magnetic force generating portion 143 assuredly act each other, and the second rotation member 120 can rotate in accordance with the rotation of the first rotation member 110.

Further, in this embodiment, the first magnetic force generating portion 141 is positioned when it is fitted to the first rotation member 110. Furthermore, the second magnetic force generating portion 143 is positioned when it is fitted to the second rotation member 120. As a result, in this embodiment, the magnetic force of the first magnetic force generation portion 141 and the magnetic force of the second magnetic force generating portion 143 can assuredly act each other.

Moreover, in this embodiment, the arrangement position of the first magnetic force generating portion 141 and the second magnetic force generating portion 143 enables assuredly coupling the insertion unit 30 side with the helical rotation member 130 by using the magnetic force. Additionally, in this embodiment, the arrangement position of the first magnetic force generating portion 141 and the second magnetic force generating portion 143 enables improving the coupling force of the insertion unit 30 side and the helical rotation member 130 by using the magnetic force.

Further, in this embodiment, the first magnetic force generating portion 141 is arranged to be adjacent to the second magnetic force generating portion 143 in the longitudinal direction and laminated on the same. As a result, in this embodiment, the insertion unit 30 can be narrowed, and the helical rotation member 130 can be assuredly rotated even though the resistance of the inner wall is produced with respect to the helical rotation member 130.

Furthermore, in this embodiment, the space portions 51b and 51c are formed by using the protruding portions 45k and 121b. As a result, in this embodiment, in the insertion unit 30 having the second rotation member 120 attached thereto, in other word in the groove portion 37, cleaning properties and sterilizing properties can be improved.

It is to be noted that, in this embodiment, the protruding portions 45k are arranged on the cylindrical member 45, and the protruding portions 121b are provided on the inner base member 121, but the present invention does not have to be restricted thereto. Such protruding portions can be arranged on at least one of the outer peripheral surface of the insertion unit 30 and the second rotation member 120, e.g., at least one of the cylindrical member 45 and the inner base member 121. Moreover, these protruding portions are arranged in such a manner that the space portions 51b and 51c communicating with the outside are formed between the second rotation member 120 and the outer peripheral surface of the insertion unit 30 when the second rotation member 120 is attached to the outer peripheral surface of the insertion unit 30, for example.

It is to be noted that, in this embodiment, the first magnetic force generating portion 141 is fitted to the first rotation member 110, and the second magnetic force generating portion 143 is fitted to the inner base member 121, but the present invention does not have to be restricted thereto.

The first magnetic force generating portion 141 may be fixed to the first rotation member 110 as long as it is arranged inside the insertion unit 30, rotated in accordance with the rotation of the first rotation member 110, and arranged in the space portion 51a while water-tightness is assured.

The second magnetic force generating portion 143 may be fixed to the second rotation member 120 as long as it is arranged outside the insertion unit 30, is adjacent to the first magnetic force generating portion 141 in the longitudinal direction, rotates the second rotation member 120 in accordance with the rotation of the first rotation member 110 including the first magnetic force generating portion 141, and is arranged in the space portion 51d while assuring the water-tightness.

[First Modification]

In the first embodiment, to improve cleaning properties and sterilizing properties of the insertion unit 30, the protruding portions 45k and 121b are arranged, and the space portions 51b and 51c are formed. However, the present invention is not restricted thereto.

Figure 6B:
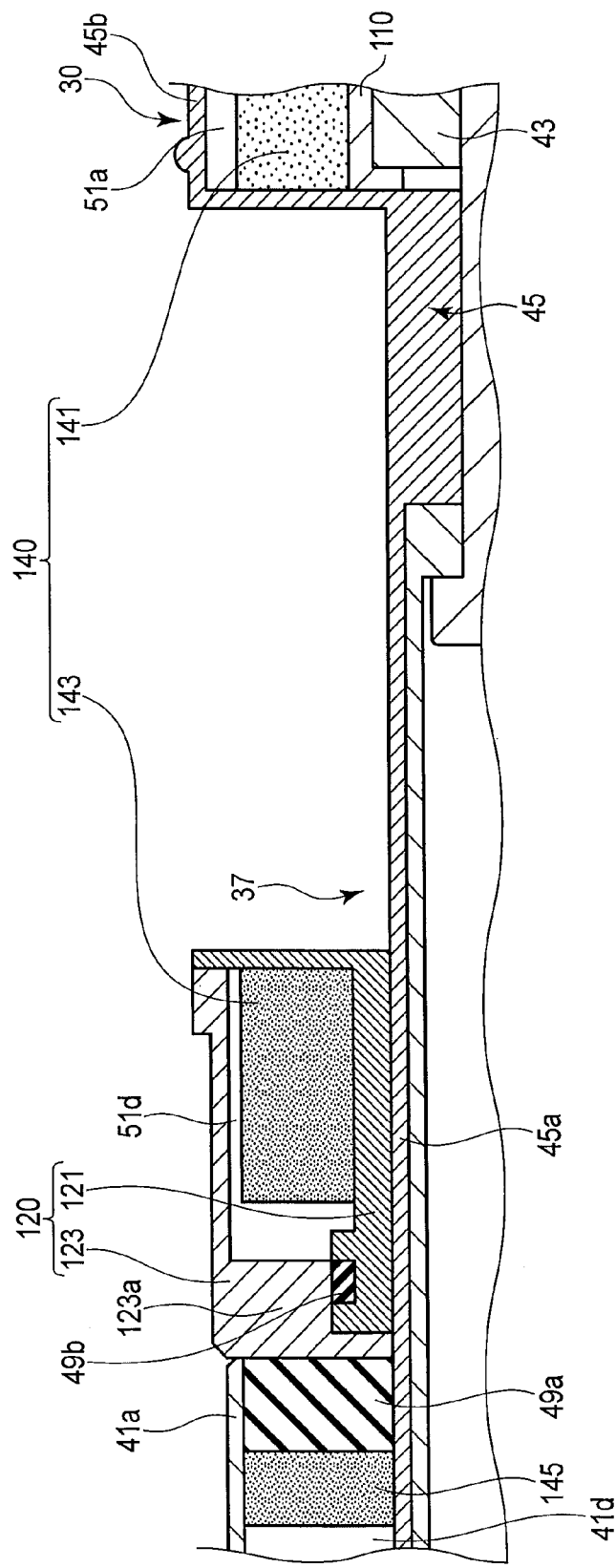
FIG. 6B is a view showing a state that a second rotation member including the second magnetic force generating portion is slid from a state depicted in FIG. 6A for cleaning and sterilization of an endoscope.

For example, as shown in FIG. 6A and FIG. 6B, the second rotation member 120 including the second magnetic force generating portion 143 is arranged so that can slide the insertion unit 30 in the groove portion 37 along the longitudinal direction.

In this case, the groove portion 37 has a length that enables the second rotation member 120 to slide in the longitudinal direction. Assuming that a length of the second rotation member 120 is L1 and a length obtained by subtracting the length L1 from the entire length of the groove portion 37 is L2, the groove portion 37 has a length that meets L2>L1.

Additionally, the grove portion 37 has a length that prevents a magnetic force of a later-described third magnetic force generating portion 145 from acting on the second magnetic force generating portion 143 in such a coupled and attached state as shown in FIG. 6A and enables maintaining the coupled and attached state.

The coupled and attached state shown in FIG. 6A means a state that the first rotation member 110 and the second rotation member 120 are attracted to each other by the magnetic force of the first magnetic force generating portion 141 and the second magnetic force generating portion 143 and the first rotation member 110 and the second rotation member 120 are adjacent to each other in the longitudinal direction and coupled with each other by the magnetic force. The coupled and attached state means a state that the helical rotation member 130 is further attached to the insertion unit 30 through the second rotation member 120 from this state.

It is to be noted that, in the coupled and attached state, as shown in FIG. 6A, the main body portion 131 is secured to the outer peripheral surface of the proximal end portion 45b of the cylindrical member 45 to cover the groove portion 37 and the second rotation member 120. At this time, for example, the main body portion 131 is caught on a protruding portion formed on the outer peripheral surface of the proximal end portion 45b, appressed against the outer peripheral surface of the proximal end portion 45b, and abuts on a taper portion formed at the distal end portion of the outer base member 123. As a result, the main body portion 131 is prevented from being displaced. The protruding portion is formed on the entire circumference of the outer peripheral surface of the proximal end portion 45b. The taper portion is formed over the entire circumference of the outer base member 123.

As shown in FIG. 6A and FIG. 6B, the magnetic force generation mechanism 140 further has, e.g., the third magnetic force generating portion 145 having a ring-like shape. The third magnetic force generating portion 145 has, e.g., substantially the same configuration as the first magnetic force generating portion 141. The third magnetic force generating portion 145 is substantially coaxially arranged with respect to the first magnetic force generating portion 141 and the second magnetic force generating portion 143. Further, the third magnetic force generating portion 145 is arranged in such a manner that the second rotation member 120 can slide in the longitudinal direction and the second rotation member 120 is interposed between the third magnetic force generating portion 145 and the first rotation member 110. Therefore, for example, the third magnetic force generating portion 145 is arranged in the groove portion 41d in a state that water-tightness is assured by the water-tightness assuring member 49a. As described above, the third magnetic force generating portion 145 is arranged inside the insertion unit 30.

As shown in FIG. 6A, the third magnetic force generating portion 145 is arranged away from the first rotation member 110 and the second rotation member 120 in the longitudinal direction so that the third magnetic force generating portion 145 is not attracted the second rotation member 120 through the second magnetic force generating portion 143 in the coupled and attached state. In other words, the third magnetic force generating portion 145 has a magnetic force that does not act on the second rotation member 120 in the coupled and attached state.

Furthermore, as shown in FIG. 6B, the third magnetic force generating portion 145 generates a magnetic force which attracts the sliding second rotation member 120 that includes the second magnetic force generating portion 143 at the time of cleaning and sterilizing the insertion unit 30, and which fixes the second rotation member 120 to a cleaning/sterilizing position apart from the first rotation member 110 in the longitudinal direction.

The cleaning/sterilizing position shown in FIG. 6B means a position at which part of the cylindrical member 45 that is a portion covered with the second rotation member 120 in the coupled and attached state is exposed and the second rotation member 120 is fixed by the magnetic force of the second magnetic force generating portion 143 and the magnetic force of the third magnetic force generating portion 145 in a state that the second rotation member 120 is adjacent to the third magnetic force generating portion 145 rather than the first rotation member 110 in the longitudinal direction.

As shown in FIG. 6B, the second magnetic force generating portion 143 and the third magnetic force generation portion 145 are arranged to be adjacent to each other in the longitudinal direction so that their magnetic forces act each other at the time of cleaning and sterilizing the insertion unit 30. Therefore, the second magnetic force generating portion 143 and the third magnetic force generating portion 145 generate magnetic forces that allow these portions to be attracted in the longitudinal direction and coupled based on the magnetic forces.

At the time of cleaning and sterilizing the insertion unit 30, for example, the helical rotation member 130 is removed from the cylindrical member 45 by the operator. Furthermore, the second rotation member 120 including the second magnetic force generating portion 143 slides the insertion unit 30 from the first rotation member 110 toward the third magnetic force generating portion 145 in the longitudinal direction by a manual operation of the operator. As a result, the part of the outer peripheral surface of the cylindrical member 45 which is the portion covered with the second rotation member 120 is exposed. Moreover, as shown in FIG. 6B, the second rotation member 120 is fixed to the cleaning/sterilizing position by the magnetic force of the second magnetic force generating portion 143 and the magnetic force of the third magnetic force generating portion 145 in a state that the second rotation member 120 is adjacent to the third magnetic force generating portion 145 in the longitudinal direction. In this state, the insertion unit 30 is cleaned and sterilized.

As described above, in this modification, when the second rotation member 120 slides, cleaning properties and sterilizing properties of the insertion unit 30 can be improved. Additionally, in this modification, at the time of cleaning and sterilization, the portion covered with the second rotation member 120 in the coupled and attached state shown in FIG. 6A can be assured exposed as depicted in FIG. 6B by using the length of the groove portion 37 and the lengths L1 and L2.

Further, in this modification, as shown in FIG. 6B, the second rotation member 120 is fixed to the cleaning/sterilizing position by the third magnetic force generating portion 145. As a result, in this modification, at the time of cleaning and sterilization, the second rotation member 120 can be prevented from being displaced, and the insertion unit 30 can be assuredly cleaned and sterilized.

[Second Embodiment]

Figure 8:
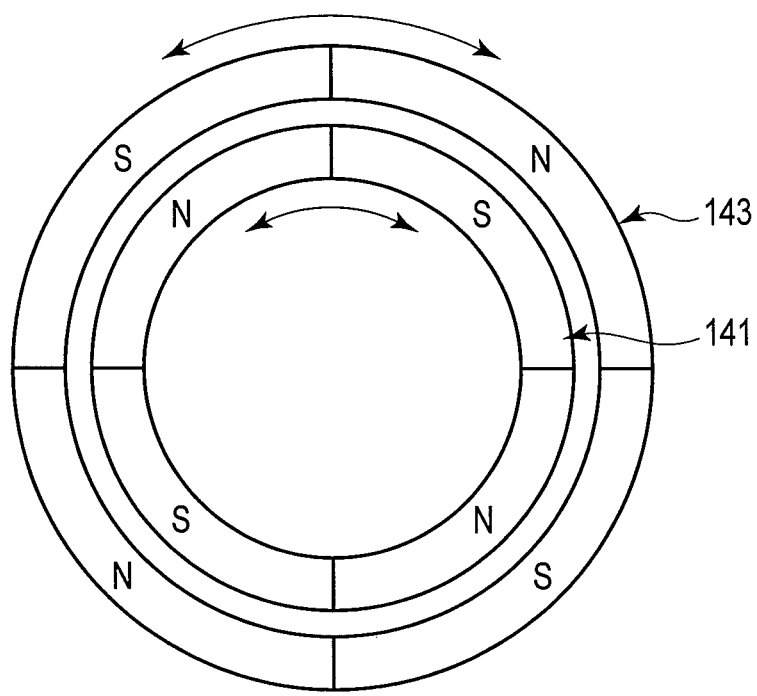
FIG. 8 is a view showing a configuration of a first magnetic force generating portion and a configuration of a second magnetic force generating portion according to the second embodiment.

A second embodiment will now be described with reference to FIG. 7 and FIG. 8. In this embodiment, structures different from those in the first embodiment alone will be explained hereinafter.

[Configuration]

As shown in FIG. 7, a second rotation member 120 including a second magnetic force generating portion 143 according to this embodiment is attached to an outer peripheral surface of an insertion unit 30 in such a manner that the second rotation member 120 including a second magnetic force generating portion 143 is adjacent to a first rotation member 110 including a first magnetic force generating portion 141 in a radial direction of the insertion unit 30, the second rotation member 120 including the second magnetic force generating portion 143 covers the first rotation member 110 including the first magnetic force generating portion 141 in the radial direction, and a central axis of the first rotation member 110 and a central axis of the second rotation member 120 are substantially coaxially arranged each other. At the same time, the second rotation member 120 is arranged so that it can freely rotate around a longitudinal axis C with respect to the insertion unit 30 including a cylindrical member 45.

As shown in FIG. 7, the second rotation member 120 is inserted into a proximal end portion 45b of the cylindrical member 45 to be adjacent to the first rotation member 110 in the radial direction of the insertion unit 30. The second rotation member 120 is positioned with respect to the proximal end portion 45b of the cylindrical member 45 by the first magnetic force generating portion 141 and the second magnetic force generating portion 143.

As shown in FIG. 7, the first magnetic force generating portion 141 and the second magnetic force generating portion 143 have, e.g., substantially the same length in the longitudinal direction each other and are arranged on substantially the same straight line in the radial direction.

As shown in FIG. 7, the first magnetic force generating portion 141 is arranged inside the insertion unit 30 and is also annularly arranged on an outer peripheral surface side of a cylindrical end portion of the first rotation member 110. The cylindrical end portion of the first rotation member 110 is inserted into a cylindrical end portion of the second rotation member 120.

Furthermore, as shown in FIG. 7, the second magnetic force generating portion 143 is annularly arranged on an inner peripheral surface side of the cylindrical end portion of the second rotation member 120. As shown in FIG. 8, the second rotation member 120 including the second magnetic force generating portion 143 is arranged on the outside of the first rotation member 110 including the first magnetic force generating portion 141 as shown in FIG. 7 in such a manner that the second magnetic force generating portion 143 covers the first magnetic force generating portion 141 in the radial direction of the insertion unit 30 as depicted in FIG. 8 and the inner peripheral surface of the second magnetic force generating portion 143 is substantially appressed against the outer peripheral surface of the first magnetic force generating portion 141.

In this embodiment, as described above, the first magnetic force generating portion 141 and the second magnetic force generating portion 143 are arranged to be adjacent to each other in the radial direction so that their magnetic forces can act each other. Therefore, when an N pole of the first magnetic force generating portion 141 and an S pole of the second magnetic force generating portion 143 are adjacent to each other and an S pole of the first magnetic force generating portion 141 and an N pole of the second magnetic force generating portion 143 are adjacent to each other, the first magnetic force generating portion 141 and the second magnetic force generating portion 143 produce magnetic forces that enables the first rotation member 110 and the second rotation member 120 to be attracted to each other in the radial direction.

Additionally, when the first rotation member 110 including the first magnetic force generating portion 141 rotates, the magnetic force of the first magnetic force generating portion 141 and the magnetic force of the second magnetic force generating portion 143 attract and repel each other. As a result, the second rotation member 120 including the second magnetic force generating portion 143 rotates in accordance with the rotation of the first rotation member 110. In other words, when the first rotation member 110 including the first magnetic force generating portion 141 rotates in a state that the first rotation member 110 and the second rotation member 120 attract each other, the first magnetic force generating portion 141 and the second magnetic force generating portion 143 generate a magnetic force that enables the second rotation member 120 to rotate in accordance with the rotation of the first rotation member 110.

Here, there is a limit in magnetic force that allows the second rotation member 120 to rotate in accordance with the rotation of the first rotation member 110. Therefore, if a resistance that is beyond expectation is produced with respect to a helical rotation member 130 when the insertion unit 30 moves forward and backward in a lumen, or if a drive force that is beyond expectation is transmitted to the rotation drive mechanism 100, the first magnetic force generating portion 141 and the second magnetic force generating portion 143 function as torque limiters, and the first rotation member 110 rotates idle with respect to the second rotation member 120.

[Effect]

As described above, in this embodiment, the same effect as that in the first embodiment can be obtained.

Further, in this embodiment, since the second rotation member 120 can be easily removed from the proximal end portion 45b of the cylindrical member 45, the cleaning properties and the sterilization properties of the insertion unit 30 can be improved.

Furthermore, in this embodiment, the longer the first magnetic force generating portion 141 and the second magnetic force generating portion 143 are in the longitudinal direction, the more strongly the magnetic force of the first magnetic force generating portion 141 and the magnetic force of the second magnetic force generating portion 143 act each other. As a result, according to this embodiment, a coupling force of the insertion unit 30 side and a helical rotation member 130 side can be further improved.

The present invention is not restricted to the foregoing embodiments as it is, and constituent elements can be modified and embodied without departing from the gist in an implementation phase. Moreover, appropriately combining the constituent elements disclosed in the foregoing embodiments enables forming various inventions.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
   an insertion unit which is inserted into a lumen and has a longitudinal axis;
   a rotation drive mechanism which is arranged inside the insertion unit;
   a tubular first rotation member which is arranged inside the insertion unit, coupled with the rotation drive mechanism, and rotates around the longitudinal axis by the rotation drive mechanism;

a tubular second rotation member which is attached to an outer peripheral surface of the insertion unit in such a manner that the second rotation member is adjacent to the first rotation member and a central axis of the first rotation member and a central axis of the second rotation member are coaxially arranged each other, and rotates around the longitudinal axis;

a helical rotation member comprising: a tubular main body portion which allows the insertion unit to be inserted therethrough and is rotatable around the longitudinal axis in accordance with rotation of the second rotation member; and a fin portion which is arranged on an outer peripheral surface of the main body portion and helically arranged around the longitudinal axis; and a magnetic force generation mechanism which is arranged in each of the first rotation member and the second rotation member and generates a magnetic force that enables the first rotation member and the second rotation member to be attracted to and coupled with each other and a magnetic force which enables the second rotation member to rotate in accordance with rotation of the first rotation member when the first rotation member rotates in a state that the first rotation member and the second rotation member are attracted to each other, wherein the magnetic force generation mechanism is arranged at a tubular end portion of the first rotation member and a tubular end portion of the second rotation member adjacent to the end portion of the first rotation member.

2. The endoscope according to claim 1, wherein the magnetic force generation mechanism comprises:

a first magnetic force generating portion annularly arranged at the tubular end portion of the first rotation member; and a second magnetic force generating portion which is annularly arranged at the tubular end portion of the second rotation member which is adjacent to the tubular end portion of the first rotation member, laminated on the first magnetic force generating portion in the longitudinal direction, and has a central axis coaxially arranged with a central axis of the first rotation member.

3. The endoscope according to claim 1, wherein the magnetic force generation mechanism comprises:

a first magnetic force generating portion which is annularly arranged on an outer peripheral surface side of the tubular end portion of the first rotation member; and a second magnetic force generating portion which is annularly arranged on an inner peripheral surface side of the tubular end portion of the second rotation member into which the tubular end portion of the first rotation member is inserted in the longitudinal direction, and arranged in such a manner that the second magnetic force generating portion covers the first magnetic force generating portion in a radial direction of the insertion unit and an inner peripheral surface of second magnetic force generating portion is appressed against an outer peripheral surface of the first magnetic force generating portion.

4. The endoscope according to claim 2, wherein the first magnetic force generating portion is formed by alternately arranging magnets having the N pole and magnets having the S pole in a circumferential direction of the first magnetic force generating portion, and the second magnetic force generating portion is formed by alternately arranging the magnets having the N pole and the magnets having the S pole in a circumferential direction of the second magnetic force generating portion.

5. The endoscope according to claim 3, wherein the first magnetic force generating portion is formed by alternately arranging magnets having the N pole and magnets having the S pole in a circumferential direction of the first magnetic force generating portion, and the second magnetic force generating portion is formed by alternately arranging the magnets having the N pole and the magnets having the S pole in a circumferential direction of the second magnetic force generating portion.

6. The endoscope according to claim 1, wherein the rotation drive mechanism comprises:

a drive member;

a shaft member which comprises a distal end portion and a proximal end portion coupled with the drive member, is inserted into the insertion unit, rotates around the longitudinal axis by a drive force of the drive member, and has flexibility; and an outer peripheral tooth portion which is arranged at the distal end portion of the shaft member and meshes with an inner peripheral tooth portion arranged in the first rotation member.

7. The endoscope according to claim 1, further comprising a protruding portion which is arranged on at least one of the outer peripheral surface of the insertion unit and the second rotation member in such a manner that a space portion communicating with the outside is formed between the second rotation member and the outer peripheral surface of the insertion unit when the second rotation member is attached to the outer peripheral surface of the insertion unit.

8. The endoscope according to claim 1, wherein the second rotation member is arranged to enable sliding the insertion unit in the longitudinal direction, and the magnetic force generation mechanism further comprises a third magnetic force generating portion which is arranged inside the insertion unit and generates a magnetic force that attracts the sliding second rotation member at the time of cleaning and sterilizing the insertion unit and fixes the second rotation member to a cleaning/sterilizing position at which the second rotating member is apart from the first rotation member in the longitudinal direction.

9. The endoscope according to claim 1, wherein the main body portion is fixed to the second rotation member.

10. The endoscope according to claim 1, wherein the main body portion is integrally formed with the second rotation member.

11. A helical rotation member which is attached to an insertion unit of an endoscope and configured to be inserted into a lumen, the endoscope comprising:

the insertion unit which is inserted into the lumen and has a longitudinal axis;

a rotation drive mechanism which is arranged inside the insertion unit;

a tubular first rotation member which is arranged inside the insertion unit, coupled with the rotation drive mechanism, and rotates around the longitudinal axis by the rotation drive mechanism;

a tubular second rotation member which is attached to an outer peripheral surface of the insertion unit in such a manner that the second rotation member is adjacent to the first rotation member and a central axis of the first rotation member and a central axis of the second rotation member are coaxially arranged each other, and rotates around the longitudinal axis; and a magnetic force generation mechanism which is arranged in each of the first rotation member and the second rotation member and generates a magnetic force that enables the first rotation member and the second rotation member to be attracted to and coupled with each other and a magnetic force which enables the second rotation member to rotate in accordance with rotation of the first rotation member when the first rotation member rotates in a state that the first rotation member and the second rotation member are attracted to each other, wherein the helical rotation member comprises:

a tubular main body portion which allows the insertion unit to be inserted therethrough and is rotatable around the longitudinal axis in accordance with rotation of the second rotation member, and fixed to the second rotation member; and a fin portion which is arranged on an outer peripheral surface of the main body portion and helically arranged around the longitudinal axis.

12. A helical rotation member which is attached to an insertion unit of an endoscope and configured to be inserted into a lumen, the endoscope comprising:

the insertion unit which is inserted into the lumen and has a longitudinal axis;

a rotation drive mechanism which is arranged inside the insertion unit;

a tubular first rotation member which is arranged in the insertion unit, coupled with the rotation drive mechanism, and rotates around the longitudinal axis by the rotation drive mechanism;

a tubular second rotation member which is attached to an outer peripheral surface of the insertion unit in such a manner that the second rotation member is adjacent to the first rotation member and a central axis of the first rotation member and a central axis of the second rotation member are coaxially arranged each other, and rotates around the longitudinal axis; and a magnetic force generation mechanism which is arranged in each of the first rotation member and the second rotation member and generates a magnetic force that enables the first rotation member and the second rotation member to be attracted to and coupled with each other and a magnetic force which enables the second rotation member to rotate in accordance with rotation of the first rotation member when the first rotation member rotates in a state that the first rotation member and the second rotation member are attracted to each other, wherein the helical rotation member comprises:

a tubular main body portion which allows the insertion unit to be inserted therethrough and is rotatable around the longitudinal axis in accordance with rotation of the second rotation member, and integrally formed with the second rotation member; and a fin portion which is arranged on an outer peripheral surface of the main body portion and helically arranged around the longitudinal axis.

* * * * *